(12) United States Patent
Heaton

(10) Patent No.: US 9,675,289 B2
(45) Date of Patent: Jun. 13, 2017

(54) METHOD AND GLUCOSE MONITORING SYSTEM FOR MONITORING INDIVIDUAL METABOLIC RESPONSE AND FOR GENERATING NUTRITIONAL FEEDBACK

(75) Inventor: Kelly Heaton, Ersigen (CH)

(73) Assignee: Roche Diabetes Care, Inc., Indianapolis, IN (US)

( * ) Notice: Subject to any disclaimer, the term of this patent is extended or adjusted under 35 U.S.C. 154(b) by 2199 days.

(21) Appl. No.: 12/665,170

(22) PCT Filed: Jun. 6, 2008

(86) PCT No.: PCT/CH2008/000254
§ 371 (c)(1),
(2), (4) Date: May 17, 2010

(87) PCT Pub. No.: WO2008/154759
PCT Pub. Date: Dec. 24, 2008

(65) Prior Publication Data
US 2011/0053121 A1    Mar. 3, 2011

(30) Foreign Application Priority Data
Jun. 18, 2007    (EP) .................................... 07405174

(51) Int. Cl.
*A61B 5/145*    (2006.01)
*A61B 5/1495*    (2006.01)
(Continued)

(52) U.S. Cl.
CPC ........ *A61B 5/1495* (2013.01); *A61B 5/14532* (2013.01); *A61B 5/7275* (2013.01);
(Continued)

(58) Field of Classification Search
USPC ........ 128/898; 435/4; 514/12, 593; 600/316, 600/300, 301, 365; 702/19; 607/301
See application file for complete search history.

(56) References Cited

U.S. PATENT DOCUMENTS 6,852,760 B1 *  2/2005  Fine et al. .................... 514/593
6,905,702 B1    6/2005  Kaufman
(Continued)

FOREIGN PATENT DOCUMENTS

| DE | 3507199 A1 | 9/1986 |
|---|---|---|
| WO | WO2004/015539 | 2/2004 |
| WO | WO2005/065538 | 7/2005 |

OTHER PUBLICATIONS

Food Product Design by Beth Hubrich, RD and Lyn O'Brien Nabors, dated Jul. 18, 2006.*

(Continued)

*Primary Examiner* — Robert J Utama
(74) *Attorney, Agent, or Firm* — Barnes & Thornburg LLP

(57) ABSTRACT

A system and method for monitoring individual metabolic response and for generating nutritional feedback involve monitoring of a glucose level in a qualified subject. The method comprises the step of consecutively performing a plurality of measurements of a glucose level in the qualified subject by a measuring device. In the measuring device first data corresponding to the measured glucose level is generated. This data is further transmitted to an analysis device. There, second data is generated representing at least one measure for variability of a glucose level of the subject from a time-series of glucose measurements represented by the first data. The second data is compared with reference data and a result of the comparison is further processed for generating a conclusion about nutritional quality of foodstuffs consumed by the subject and/or about a risk of long-term health complications of the subject. Finally, feedback is provided corresponding to the conclusion on an output device.

27 Claims, 8 Drawing Sheets

(51) Int. Cl.
*G06F 19/00* (2011.01)
*A61B 5/00* (2006.01)

(52) U.S. Cl.
CPC ........ *G06F 19/324* (2013.01); *G06F 19/3406* (2013.01); *G06F 19/3418* (2013.01); *G06F 19/3475* (2013.01); *A61B 5/0031* (2013.01); *A61B 5/742* (2013.01)

(56) References Cited

U.S. PATENT DOCUMENTS

| | | | |
|---|---|---|---|
| 6,923,763 B1 | 8/2005 | Kovatchev et al. | |
| 6,949,070 B2* | 9/2005 | Ishler | 600/365 |
| 7,029,444 B2* | 4/2006 | Shin | A61B 5/14532 600/316 |
| 2003/0208110 A1* | 11/2003 | Mault et al. | 600/300 |
| 2003/0208113 A1* | 11/2003 | Mault et al. | 600/316 |
| 2003/0212317 A1* | 11/2003 | Kovatchev et al. | 600/365 |
| 2004/0142403 A1* | 7/2004 | Hetzel et al. | 435/14 |
| 2004/0193025 A1* | 9/2004 | Steil et al. | 600/316 |
| 2005/0043894 A1* | 2/2005 | Fernandez | 702/19 |
| 2005/0113650 A1* | 5/2005 | Pacione et al. | 600/300 |
| 2005/0181354 A1* | 8/2005 | Estep, III | 435/4 |
| 2005/0182308 A1* | 8/2005 | Bardy | 600/300 |
| 2005/0244910 A1 | 11/2005 | Wolever et al. | |
| 2006/0253259 A1* | 11/2006 | Fernandez | 702/19 |
| 2007/0060803 A1* | 3/2007 | Liljeryd et al. | 600/301 |
| 2007/0106333 A1* | 5/2007 | Fernandez | 607/2 |
| 2007/0111933 A1* | 5/2007 | Kopchick et al. | 514/12 |
| 2008/0004904 A1* | 1/2008 | Tran | 705/2 |
| 2008/0214910 A1* | 9/2008 | Buck | 600/310 |
| 2008/0294012 A1* | 11/2008 | Kurtz et al. | 600/300 |
| 2008/0314395 A1* | 12/2008 | Kovatchev et al. | 128/898 |
| 2009/0171589 A1* | 7/2009 | Kovatchev | 702/19 |
| 2010/0285082 A1* | 11/2010 | Fernandez | 424/422 |
| 2010/0332445 A1* | 12/2010 | Ray et al. | 706/54 |
| 2011/0054439 A1* | 3/2011 | Yodfat et al. | 604/503 |
| 2011/0071765 A1* | 3/2011 | Yodfat et al. | 702/19 |
| 2012/0197621 A1* | 8/2012 | Jain | 703/11 |
| 2012/0266251 A1* | 10/2012 | Birtwhistle et al. | 726/26 |
| 2014/0012511 A1* | 1/2014 | Mensinger et al. | 702/19 |

OTHER PUBLICATIONS

International Search Report for PCT/CH2008/000254, completed Jul. 29, 2008.
Bolli, Geremia B., "Glucose Variability and Complications", Jul. 2006, *Diabetes Care*, vol. 29, No. 7, pp. 1707-1709.
Brownlee, Michael, et al., "Glycemic Variability: A Hemoglobin $A_{1c}$-Independent Risk Factor for Diabetic Complications", Apr. 12, 2006, *Journal of the American Medical Association*, vol. 295, No. 14, pp. 1707-1708.
Close, Kelly L., "Diabetes Close Up on Glycemic Variability", Dec. 2005, *Diabetes Close Up*, No. 54, pp. 1-27.
Hirsch, Irl B., et al., "Should Minimal Blood Glucose Variabilty Become the Gold Standard of Glycemic Control", 2005, *Journal of Diabetes and Its Complications*, No. 19, pp. 178-181.
Hirsch, Irl B., et al., "Is AIC the Best Measure of Glycemic Control?", 2005, *Business Briefing: North American Pharmacotherapy*, pp. 44-48.
Hirsch, Irl B., "Glycemic Variability: It's Not Just About AIC Anymore!", 2005, *Diabetes Technology & Therapeutics*, vol. 7, pp. 780-783.
Monnier, Louis, et al., "Activation of Oxidative Stress by Acute Glucose Fluctuations Compared With Sustained Chronic Hyperglycemia in Patients With Type 2 Diabetes", 2006, *Journal of the American Medical Association*, vol. 295, No. 14, pp. 1681-1687.
Murphy, Josh, "Risk Factors: Acute Glycemic Variability Correlates with Oxidative Stress", May 4, 2006, Diabetes and Vascular Education, C:\Documents and Settings\ezc\Local Settings\Temporary Internet Files\OLK9E\Murphy2006Acute.htm.

* cited by examiner

METHOD AND GLUCOSE MONITORING SYSTEM FOR MONITORING INDIVIDUAL METABOLIC RESPONSE AND FOR GENERATING NUTRITIONAL FEEDBACK

CROSS-REFERENCE TO RELATED APPLICATIONS

This application is a U.S. national counterpart application of International Application Serial No. PCT/CH2008/000254, filed Jun. 6, 2008, under 35 USC §371, which claims priority to European Patent Application Serial Number 07405174.9, filed on Jun. 18, 2007, the entire disclosure of both are hereby incorporated herein by reference.

TECHNICAL FIELD

The present disclosure relates to a method for monitoring individual metabolic response and for generating nutritional feedback. The present disclosure further relates to a glucose monitoring system for carrying out the method as well as to a computer program product for carrying out the method.

BACKGROUND

After ingestion of food or beverages that contain carbohydrates, these carbohydrates are broken down during digestion and thereby converted to mono- and disaccharides, mostly glucose. Glucose is a source of energy for the cells of the organism. This energy is yielded within the cells through glycolisis and subsequent reactions of the citric acid cycle. Glucose is transported to the cells via the organism's blood stream. Therefore, ingestion of food will have an influence on the concentration of glucose within the blood stream; i.e. the blood glucose level will change.

There is significant evidence that a calorie-restricted diet promotes good health (U.S. National Institute on Aging, Primate Aging Study). Humans are recommended to receive between 45-65% of daily caloric intake from carbohydrates. Therefore, one benefit of a calorie-restricted diet is an overall reduction of blood glucose levels. High blood glucose concentrations have been correlated with numerous health problems including oxidative stress, micro- and macro-vascular tissue damage, heart disease, hypertension and Type II diabetes.

Certain carbohydrate-containing foods are rapidly absorbed into the blood stream, causing a rapid increase of blood glucose levels and acutely over-supplying the body with energy. Such carbohydrates, as refined flour or pure glucose, require very little digestion to release their sugars and are therefore rapidly absorbed into the blood, often at a rate which exceeds the body tissue's ability to metabolize the excess energy. Carbohydrates which are more difficult to digest or to absorb appear in the blood stream at a slower pace following ingestion; and are therefore less likely to cause a significant rise in blood glucose levels. However, any meal that contains a large quantity of carbohydrates will eventually result in elevated blood glucose, as the body's rate of metabolism lags behind the inevitable release of sugars from food in the gut. The hyperglycemic effect of excess carbohydrate consumption is more pronounced in individuals who suffer from insulin resistance and/or impaired glucagon supression, conditions that characterize Metabolic Syndrome and Type II diabetes. Even in healthy individuals, meals that contain large quantities of rapidly absorbed carbohydrates can result in a fast rise of blood glucose followed by a rapid decline (evidence of higher circulating insulin concentrations in response to the glucose spike).

The medical significance of the magnitude of blood glucose fluctuations is a controversial topic that has been the subject of extensive research (see e.g. G. Bolli, "Glucose Variability and Complications.", Diabetes Care, Vol. 29, No. 7, July 2006 (Editorial); M. Brownlee, "Glycemic Variability: A Hemoglobin A1c-Independent Risk Factor for Diabetic Complications." (Reprinted) JAMA, Apr. 12, 2006—Vol 295, No. 14. pp. 1707-1708; K. Close, Diabetes Close Up, December 2005, No. 54, DCU on Glycemic Variability; B. Hirsch et al., "Should minimal blood glucose variability become the gold standard of glycemic control?" Journal of Diabetes and Its Complications.", Vol. 19 (2005) pp. 178-181; I. Hirsch, "Is A1c the Best Measure of Glycemic Control?" Business Briefing, North American Pharmacotherapy. 2005; I. Hirsch, "Glycemic Variability: It's Not Just About A1C Anymore!" Diabetes Technology & Therapuetics, Vol. 7, No. 5, 2005; L. Monnier et al., "Activation of Oxidative Stress by Acute Glucose Fluctuations Compared With Sustained Chronic Hyperglycemia in Patients With Type 2 Diabetes.", JAMA 2006; 295:1681-1687; J. Murphy, "RISK FACTORS: Acute Glycemic Variability Correlates With Oxidative Stress." 2005 DiaVed, Inc. May 2006).

Potential consequences of chronic high glycemic fluctuations cited in the literature include an increased risk of Type II diabetes, hypertension and heart disease. A causal link between the magnitude of glycemic fluctuations and the risk of chronic disease is supported by clinical evidence of increased free radical production at the cellular level, resulting in vascular tissue damage. High levels of glycemic fluctuation have also been associated with hyperinsulinemia, mood swings, appetite stimulation, fatigue and compromised athletic performance. Severe fluctuations in blood sugar have further been correlated with hunger pangs (see e.g. U.S. Pat. No. 6,905,702, Los Angeles Children's Hospital) and chronic health problems; frequent fluctuations with high amplitude have been correlated with oxidative stress, micro- and macro-vascular tissue damage.

Therefore, a meal will preferably release carbohydrates into the blood slowly, producing a gradual rise that is manageable by the body's tissues. For these reasons, also to promote appetite control and safety for people trying to lose weight, nutritionists Jenny Brand-Miller and Thomas Wolever recommend a diet that minimizes the magnitude of glycemic response.

There are different ways of quantifying the progression of a glucose level in an individual. One aspect of the change of the concentration of glucose relates to the rate at which the ingested food or beverage is able to increase the blood glucose level and the length of time the blood glucose remains elevated. This is usually denoted by the term "glycemic response".

There are established metrics to evaluate the glycemic impact of carbohydrate-containing foods, namely the Glycemic Index (GI) and the Glycemic Load (GL). The Glycemic Index (GI) is proportional to the area under the curve (AUC) when blood glucose concentration is plotted against time, wherein only the two hours following the ingestion of a fixed portion of carbohydrate (usually 50 g) are considered. The AUC of the test food is divided by the AUC of a reference food portion (either glucose or white bread) of equal carbohydrate content and multiplied by 100. The average GI value is calculated from data collected in a sample population and is available in GI tables (e.g. J. Brand-Miller, K. Foster-Powell, "Shopper's Guide to GI Values", Marlowe & Company, 2007). Glycemic Load (GL) takes into account the portion size of the ingested food. It is calculated as the quantity (in grams) of its carbohydrate content, multiplied by its GI, and divided by 100.

In summary, glycemic response relates to the quantitative aspects of the development of the glucose level, i.e. to the rate at which the ingested food or beverage is able to increase the blood glucose level and the length of time the blood glucose remains elevated. The usual measures are based on AUC which primarily quantifies the amount of carbohydrates consumed.

However, two progressions of the glucose level in a subject may have a completely different shape but still correspond to the same AUC value. Therefore, AUC cannot provide the full picture. Besides the merely quantitative aspects described above there are further aspects of a more qualitative nature, relating to the "quality" of the glucose response, generally to how much a person's blood sugar fluctuates over time, and therefore to the quality of carbohydrates consumed. For example, pure refined sugar is known to cause a spike in blood glucose followed by a rapid decline. It is therefore reasonable to assume that a measured spike and decline in blood glucose is indicative of food consumption in which the food contained a high portion of fast-acting carbohydrates.

From the field of diabetes care methods are known for quantifying the degree of fluctuation in a glucose concentration in the bloodstream or interstitial fluid over time, especially during the time following a meal or another glucose-altering event such as physical activity or hormone level changes. For the purposes of this document, these methods and the quantitative measures they provide are denoted by the general term Glycemic Variability (GV). GV characterizes the fluctuations (frequency and magnitude) of the glucose concentration.

For the purpose of assessing GV, the glucose response may be monitored by spot blood glucose measurements (SMBG), such as e.g. one month of routine self-monitoring data, or by continuous glucose monitoring (CGM) with much higher measurement frequencies, see e.g. the following articles by B. Kovatchev et al.: "Methods for Quantifying Self-Monitoring Blood Glucose Profiles Exemplified by an Examination of Blood Glucose Patterns in Patients with Type 1 and Type 2 Diabetes.", Diabetes Technology & Therapuetics, Vol. 4, No. 3, 2002; "Algorithmic Evaluation of Metabolic Control and Risk of Severe. Hypoglycemia in Type 1 and Type 2 Diabetes Using Self. Monitoring Blood Glucose Data.", Diabetes Technology & Therapuetics, Vol. 5, No. 5, 2003; "Quantifying Temporal Glucose Variability in Diabetes via Continuous Glucose Monitoring; Mathematical Methods and Clinical Application.", Diabetes Technology & Therapuetics, Vol. 7, No. 6, 2005; "Evaluation of a New Measure of Blood Glucose Variability in Diabetes.", Diabetes Care, Vol. 29, No. 11, November 2006. pp. 2433-2438.

There are numerous published metrics to quantify different aspects of glycemic variability, both during a single day (e.g. CONGA, see C M McDonnell et al. "A Novel Approach to Continuous Glucose Analysis Utilizing Glycemic Variation.", Diabetes Technology & Therapuetics, Vol. 7, No. 2, 2005) and also over longer periods of time (i.e. LBGI/HBGI, see B. Kovatchev et al., "Algorithmic Evaluation of Metabolic Control and Risk of Severe Hypoglycaemia in Type 1 and Type 2 Diabetes Using Self-Monitoring Blood Glucose Data," Diabetes Technology and Therapeutics, Volume 5, Number 5, 2003. pp. 817-828).

To date, there is no method of GV that is accepted in the clinical practice of diabetes care, although there exists growing interest in the medical relevance (and controversy, see Kilpatrick et al. 2006). GV can be used to describe general trends over long periods of time, compatible with the long time monitoring of HBA1c; or to focus on events of short duration, such as meals or overnight. The results of a determination of glycemic variability may be used to predict health risks for the patient, such as the patient's risk of hypoglycemia, including intra-day risk, intra-week risk or a general risk of hypoglycemia. Furthermore, GV may be correlated with the other health risks described above, such as oxidative stress and macro- or micro vascular tissue damage. Similarly, GV may also provide a way to stage Type II diabetes, i.e., "less stability indicates less metabolic control."

In summary, today GV is considered to be a way of assessing the quality of diabetes control. However, clinicians do not agree on what "good" control is. Because of this, it is difficult to define a universal metric. The only references available are the measurements performed on healthy patients. A therapy is "good" if it leads to glucose excursions similar to the ones observed in healthy patients.

However, despite the fact that the blood sugar fluctuations do not only affect the health of diabetic people but also of the health of individuals who do not suffer uncontrolled metabolic disorders and do not require exogenous insulin, the potential of GV has not yet been fully exploited outside the field of diabetes care. Whereas the quantity of the carbohydrates consumed can be partly taken into account by using GI or GL tables, the glycemic variability is not systematically observed. Despite the wealth of literature available on metabolism and nutrition, the actual physiological effect of actual ingested meals (both food composition and quantity) remains a largely speculative "guessing game," leading to widespread confusion, denial and frustration among dieters. This is also true for the use of GL tables which bases on the assumption that all labeled food items are assumed to have the same effect on the blood glucose level of any consumer. As stated by Connie Gutterson in her article "Syndrome X: Prescribing the Right Carbohydrates", "it is the quality of the foods consumed that will impact long term health. It is our professional responsibility to address this but to also provide the link between science and food."

SUMMARY

A system and method for monitoring individual metabolic response pertaining to the technical field initially mentioned, that is comfortable for the user and that provides a personalized and specific feedback supporting the user's dietary management is disclosed.

According to the present disclosure, a method for monitoring individual metabolic response and for generating nutritional feedback involves monitoring of a glucose level in a qualified subject and may comprise the steps of:

a) consecutively performing a plurality of measurements of a glucose level in the qualified subject by a measuring device;
b) in the measuring device generating first data corresponding to the measured glucose level;
c) transmitting the first data to an analysis device;
d) in the analysis device generating second data representing at least one measure for variability of a glucose level of the subject from a time-series of glucose measurements represented by the first data;

e) comparing the second data with reference data and further processing a result of the comparison for generating a conclusion about nutritional quality of foodstuffs consumed by the subject and/or about a risk of long-term health complications of the subject; and
f) providing feedback corresponding to the conclusion on an output device.

Correspondingly, a glucose monitoring system for monitoring glycemic individual metabolic response in a qualified subject and for generating nutritional feedback may comprise:
a) a measuring device comprising a sensor for consecutively performing a plurality of measurements of a glucose level in the qualified subject and comprising a data generator for generating first data corresponding to the measured glucose level;
b) an analysis device comprising a computer to generate second data representing at least one measure for variability of the glucose level of the subject from a time-series of glucose measurements represented by the first data, and to compare the second data with reference data and for further processing a result of the comparison for generating a conclusion about nutritional quality of foodstuffs consumed by the subject and/or about a risk of long-term health complications of the subject; and
c) a computer-controlled output device to provide feedback corresponding to the conclusion.

Steps d) and e) of the method may be carried out by a computer program product that includes program code which when executed on an analysis device may carry out the following steps:
a) generating second data representing at least one measure for variability of a glucose level of a qualified subject from a time series of glucose measurements represented by first data;
b) comparing the second data with reference data;
c) generating a conclusion about nutritional quality of foodstuffs consumed by the subject and/or about a risk of long-term health complications of the subject, based on the result of the comparison.

In the context of the disclosure, a subject may be qualified if it has a stable fasting glucose level without having to use exogenous insulin, i. e. a qualified subject is a human or animal who possesses the natural ability to metabolize carbohydrates without the use of exogenous insulin (in contrast to people suffering Type I diabetes, for example). This allows for obtaining meaningful results from the comparison of the second data with reference data and for generating a meaningful conclusion about the nutritional quality of the foodstuffs in relation to the subject and/or about a risk of long-term health complications of the subject.

In the context of the disclosure, suitable frequencies for the consecutive measurements of the glucose level may start from at least 1 measurement a day (in the case of SMBG) and go up to 60 measurements an hour and more (in the case of CGM). Suitable CGM measurement frequencies range from 4 to 60 measurements an hour. The optimum frequency of measurements depends on the chosen measure for glycemic variability, i. e. measures that relate to short time properties of glycemic variability will in general require higher frequencies than measures relating to long time properties. The glucose level may be measured in any measurable tissue compartment, e. g. in blood or interstitial fluid. In principle, non-invasive methods of glucose monitoring are also acceptable in the context of this invention, as soon as a sufficient measuring accuracy can be achieved. The measuring device and/or the analysis device and/or the output device may be integrated into one single unit or they may be comprised by different units or even distributed to several units.

The generation of the first data may include converting the output of the actual sensor component into a signal (e. g. an analog or digital signal in the form of a voltage) that may be transmitted to the analysis device. The first data generation may involve further conversion of the sensor output. The generation step may happen within a usual sensor device or within a circuit or computing unit of the measuring device.

A measure for variability of the glucose level of the subject quantifies the frequency, the distribution of patterns and/or the magnitude of the fluctuations of the glucose level. It is based on a time-series of glucose measurements, i.e. on at least two, preferably at least three glucose measurements (or time-glucose data pairs, respectively). Besides the values themselves their temporal order and/or distribution may be taken into account. The measure may be based directly on the measured values, on a function which represents these values (e.g. a functional fit) and/or on the first derivative (slope) or higher derivatives of such a function or the values themselves (gained from the values by well-known numerical techniques). The measure may be obtained from these quantities by statistical and/or functional analysis.

The reference data may correspond to a target value which represents the value of the chosen measure for an optimally working metabolism of the subject. It may consist of a single value or of a range, which is e.g. delimited by lower and/or upper target levels for the value of the measure. The target value or range may be different in different time periods. Advantageously, the reference data is stored in a storage of the analysis device. Preferably, the reference data is established by a healthcare professional nutritionist, based on individual attributes of the subject and/or on medical/nutritional examinations of the subject.

The comparison step may involve a simple comparison between two values (such as determined measure against target value), or it may involve the comparison of a plurality of values, e.g. involving a number of different measures and/or the same measure determined for different time intervals. The result of the comparison may as well consist of just a single statement (above/below target) or more detailed information, such as a rate of correlation or a number of statements for different measures and/or time intervals.

Within the disclosed method or system this result of the comparison is further processed in order to generate the conclusion about the nutritional quality of the foodstuffs consumed by the subject and/or about the risk of health complications. In a simple case, a single value relating to the magnitude of fluctuation of the glucose level during a time interval after a meal may be compared to a target value. If the measure is larger than the target value it will be concluded that the meal contained too many carbohydrates that are rapidly absorbed into the blood stream of the subject. In a more complicated case, a number of values may be compared to respective target ranges. The results of this comparison may further be used to generate a profile for a number of health risks.

The disclosed method and system will provide the subject with real-time information about their individual glycemic variability as well as about the adequacy of food choices, physical exercise and further lifestyle choices.

The result may be displayed in numerical form, e.g. as absolute values, ratios, fractions, decimal fractions or percentages, and/or in graphical form. Generally, the measure will be determined for a given time interval, which may correspond to days or weeks other (meaningful) time intervals (such as a typical time period following a meal). Instead of or additional to visual display all of the aforementioned information may be communicated by auditory output or other communication means.

It should be appreciated that the subject can precisely monitor its patterns of glycemic response and thereby learn the actual consequences of ingested food and beverage. Monitoring the glucose level is also an excellent method for revealing the metabolic effects of exercise, an important aspect of any weight management or healthcare program. The subject is therefore enabled to monitor the effect of consumed food and beverage on individual glycemic response for the benefit of nutrition, sport, health and/or weight loss management. The disclosure provides a system and method for diagnosing individual glycemic variability and utilizing this diagnosis as the basis for nutritional feedback. Dietary feedback is based on measured, analyzed patterns of glucose and administered according to widespread knowledge of human metabolism as described in the scientific, medical and nutritional literature. The disclosed method and system are may therefore be used as tools for supporting weight management, nutritional counseling and preventive medicine.

The benefits of recording the personal response to diet and exercise are numerous, including improved knowledge of the individual's body, motivation and learning the effects of behavior, especially concerning food choices, on the individual's metabolism. For dieters, athletes (competitive as well as recreational) that aim at improving their athletic performance, or other people that have to take care of their blood glucose levels (such as people with obesity, hypertension or risk of diabetes), employing the disclosed method provides a much more valuable source of information than just the caloric content or Glycemic Index of foods, which are intrinsic properties of food and do not correlate directly with individual metabolic response and which do not provide any direct information about the variability of the glucose response. Nor does food labeling provide direct, personal feedback about the subject's body, choices or history (change over time). Different people react differently to the same foods, especially under real life conditions of overlapping meals, stress, variable physical activity, medication, hormonal changes and hydration.

The disclosed method and system allow for an optimized dietary and behavioral management, wherein food choices can be entirely customized to the individual's needs instead of being dictated by nutritional guidelines, food labeling, popular theories or fad diets. The disclosure offers a unique way to educate and motivate people in their dietary and exercise goals.

In a one embodiment for generating the second data, the at least one measure for variability is calculated for first data representing two different time intervals yielding a first result and a second result. Subsequently, the first result and the second result are considered for comparing the second data with the reference data and for further processing the result of the comparison for generating the conclusion. The two time intervals may partly or fully overlap, however, they should not be identical. In the simplest case each time interval is represented by a single measurement of the glucose level. Employing glucose data relating to two distant intervals in time is particularly advantageous if the long-term behavior of the glucose progression is to be studied. Inter alia, it is part of the MODD and CONGA metrics described below.

The method may further comprise the step of providing suggestions regarding how to achieve personal metabolic goals. These suggestions may be based on the comparison of the second data with the reference data and/or on other quantities, e.g. obtained by further statistical analyses of the glycemic response curves. The suggestions may relate to the choice of foods, portion sizes, times of meals, intensity of physical exercise and may include alerts if certain unfavorable situations (adverse food choices or meal times etc.) are detected by the measurement device and method as well as a sort of gratification system rewarding positive developments.

The analysis as well as the provision of suggestions as mentioned before may be controlled and effected by supplementary software tools to aid in the real-time and/or retrospective interpretation of the measured glycemic data. For this purpose, the system may connect to a database of nutritional and/or health guidelines, e. g. via a data network such as the internet. Furthermore, it may have the possibility to connect to a web-enabled site for social networking, i. e. related to nutritional topics, weight loss, sports or diabetes.

Glucose levels, especially their absolute values, differ from subject to subject. If a measure for glycemic variability is used that does not purely depend from relative values or slopes it is therefore advantageous if a reference level is established that allows for accommodating the individual situation of the subject.

In the case of continuous glucose monitoring, due to sensor drift and other sources of error, it will be necessary to regularly calibrate the sensor. Conventionally, this is done by performing spot measurements of the blood glucose level, e.g. by employing a conventional strip glucose meter. However, these measurements ask for an additional effort of the user.

Therefore, in the case of continuous glucose monitoring the method may comprise a step of self-calibration for the measuring device, comprising the step of establishing a glucose reference level of the subject, to be used as a reference for generating the second data, for comparing the second data with the reference data and/or for further processing the result of the comparison for generating the conclusion. Thereby, calibration with independent blood glucose measurements may be minimized or avoided.

The glucose reference level may correspond to a fasting glucose level of the subject. In this case, the disclosure method may comprise the step of self-calibration for the measuring device, during which the fasting glucose level of the subject is established.

The step of self-calibration may be automatically and regularly effected during periods without ingestion of foods and glucose-affecting beverages by the subject, in particular regularly overnight. This may assure that the calculated fasting glucose level is continuously calibrated against the measured fasting glucose level. It is possible to perform the step of self-calibration based on a time signal (e. g. every 24 hours, regularly at 05:00 in the morning) and/or it may be performed ex post, after the device has established a long enough period without glucose-relevant ingestion of foods and beverages, based on the performed glucose measurements (cf. EP 1 728 468 A1, F. Hoffmann-La Roche AG, Roche Diagnostics GmbH).

In one embodiment, the step of self-calibration comprises the following substeps
a) monitoring the subject's glucose level during a minimum of six, in particular during a minimum of eight, consecutive hours without ingestion of foods and beverages;
b) determining when glucose has stabilized at a fasting level c) averaging a signal corresponding to a measured glucose concentration during an interval of greatest signal stability in order to determine the reference data corresponding to the fasting glucose level.

The length of the interval may be predetermined, e.g. 2 hours. It is chosen from the whole measuring period by using statistical methods such as running averages or a standard deviation of the measured glucose values or of the glucose rate-of-change, respectively. One possible method to determine signal stability is described in EP 1 728 468 A1 (F. Hoffmann-La Roche AG, Roche Diagnostics GmbH).

What is determined from these steps is the value of the sensor signal corresponding to the user's fasting glucose level. This value is later used as a reference data for converting the measured values of the sensor signal when monitoring the subject's glucose level and when calculating the second data, e. g. when prandial glucose is measured against fasting glucose for the purpose of calculating iAUC. It should be appreciated that it is generally not necessary to know the absolute value of the subject's fasting glucose level (say the actual value in mg/dl) but only the difference of the actual glucose level and the fasting glucose level. Therefore, for calculating most of the measures discussed below, it is possible not to use the absolute glucose value as an input parameter but the difference between the glucose value and the glucose fasting level. This is in contrast to diabetes management where usually the absolute value has to be determined.

If it is noticed during the process of self-calibration that the glucose level rises due to the user having a meal or drink and/or that a stable fasting glucose level is not reached, the value of the previous self-calibration step will be used until a later self-calibration is successful.

Instead of carrying out a self-calibration step, the reference fasting glucose level may be established by a conventional fasting glucose measurement (using e.g. a strip-based glucose meter), i.e. in the morning before breakfast or after more than eight hours of no food consumption.

Instead of the fasting glucose level, other reference levels may be employed, e. g. a longtime average of the subject's glucose level. Instead of establishing the value in the context of the method or system, this reference value may be measured by employing usual methods known from the prior art, e. g. by spot blood glucose measurements, and entered into the device by the user, its healthcare provider or nutritionist.

In one embodiment for generating the second data a mean value and/or a standard deviation of glucose level measurements represented by the first data and/or of quantities derived from the first data is calculated. The mean value and standard deviation may be easily determined. For example, these measures are employed for calculating the coefficient of variation (CV) or J-index metrics.

Additionally or alternatively, for generating the second data a standard deviation of a slope of a function representing the time-series of glucose measurements represented by the first data may be calculated. The standard deviation of the slope itself is a suitable measure for glycemic variability. Still, it is possible to further process the value of the standard deviation of the slope to get further measures.

Alternatively, for generating the second data a difference between a first glucose measurement taken in the morning and a second glucose measurement taken in the evening preceding or following said morning is calculated. Again, both glucose measurements are represented by the first data. In particular, these measurements may be constituted by usual spot measurements performed by the user. It is a benefit of this approach that only two BG measurements are required per day: once when the individual wakes up, and once when the individual goes to sleep. For the user, this is easy to remember and does not require the use of CGM devices. However, in principle one could also use the method with data collected by a CGM device.

We denote the morning measurements as $MM_d$ where d denotes the day of the measurement, correspondingly the evening measurements are denoted as $EM_d$. This allows us to calculate two useful indices of individual glucose levels, the Daily Glucose Differential (DGD) and the Overnight Glucose Differential (OGD), where $$DGD = EM_d - MM_d; \text{ and}$$

$$OGD = EM_{d-1} - MM_d,$$

i.e. the Daily Glucose Differential (DGD) measures the difference between the glucose level of the individual measured in the evening of a given day and the glucose level measured in the morning of this given day. The DGD indicates the degree of an individual's glucose elevation just prior to sleep, or the accumulated glycemic impact of an individual's food consumption, base metabolic rate and physical activity during a day. Ideally, for optimal metabolic health, an individual will awake in the morning at fasting glucose levels and go to sleep in the evening at fasting glucose levels (or near fasting). If an individual's final measurement of the day, $EM_d$, is much larger than his/her first measurement in the morning, $MM_d$, this indicates that the individual has either (1) consumed more than recommended for weight loss, primarily in the evening; or (2) the individual has eaten too soon before sleep. Researchers have observed that overweight people are strongly correlated with overeating in the evening, even if these individuals eat normal or restricted calorie meals during the rest of the day (see The Journal of Nutrition, January 2004. Physiology & Behavior, 1987, vol 40. Journal of the American Dietetic Association, December 1994. Body Mass Index New Research, 2005. Shanthy Bowman, PhD, U.S. Department of Agriculture's Agricultural Research Service. John M. de Castro, PhD, chairman, department of psychology, University of Texas, El Paso. Edward Saltzman, MD, energy metabolism scientist, Jean Mayer USDA Human Nutrition Research Center on Aging, Tufts University, Boston). Therefore, the Daily Glucose Differential is a useful metric for providing diagnostic feedback for people trying to lose weight.

The Overnight Glucose Differential (OGD) stands for the difference between the glucose level measured in the morning of a given day and the glucose level measured in the evening of the day before. Due to the fact that the glucose concentration is expected to remain static or to decrease during the night, the measure has been defined such that the resulting value tends to be positive rather than negative. The OGD is a useful indication of an individual's resting metabolic rate. A comparison of the morning glucose level MK, with the glucose level $EM_{d-1}$ from the night before provides valuable information about an individual's ability to metabolize circulating glucose during a known time period of fasting and rest. OGD is most useful when a true fasting reference value for the individual is known; and also when the metric can be calculated for more than one overnight period, such as during several nights, wherein the calculated OGD values can be compared to identify trends in overnight glucose control. Individuals with an elevated evening glucose level who do not return to fasting glucose by the following morning may suffer from (1) excessive nighttime overeating, either at dinner or during the night; and/or (2) impaired metabolic function wherein the body at rest is unable to dispose of excess glucose.

The calculated value of both indices DGD and OGD would ideally be zero. However, it is expected that both the Daily Glucose Differential as well as the Overnight Glucose Differential would tend towards a positive value, based on the metric described. The two values should be the same or similar. For healthy people, consecutive days of Daily Glucose Differential and Overnight Glucose Differential are expected to yield the same value because both compare the same evening's post-prandial glucose against morning fasting glucose (theoretically, a healthy person's glucose is stable from morning to morning).

As long as an individual's fasting glucose level is always within a similar fasting range, his or her body is able to handle the excess glucose of whatever food has been ingested the evening before. If the fasting (morning) glucose varies, this may be an indicator of health problems.

Generally, normal fasting glucose levels for healthy people range from 70-99 mg/dL. Measurements of 100-125 mg/dL indicate elevated glucose (this range is common and normal for post-prandial values, but not for fasting; fasting glucose of these levels is an indicator of pre-diabetes or diabetes.) Values of 126-170 mg/dL indicate highly elevated glucose (this range is infrequent, but still normal for post-prandial values). However, fasting values that high are a certain indicator of diabetes. Values above 170 mg/dL may indicate the presence of a metabolic disorder, even when recorded post-prandially.

A morning measurement ($MM_d$) outside of the fasting glucose range should never occur for a healthy individual. If it does, the presence of a metabolic disorder may be indicated.

Assuming that $MM_d$ values will always fall within the fasting range, the magnitude of calculated differentials depend upon the evening measurement ($EM_d$) value. To calculate the significance of a non-zero Daily Glucose Differential, we can apply the following ranges (assuming $EM_d$ and $MM_d$ are both from the same day):

$EM_d - MM_d \leq 5$ mg/dL: ideal;

5 mg/dL $< EM_d - MM_d \leq 15$ mg/dL: slightly elevated;

15 mg/dL $< EM_d - MM_d \leq 25$ mg/dL: elevated;

$EM_d - MMd > 25$ mg/dL: very elevated

The Overnight Glucose Differential requires slightly different interpretation. On the one hand, we would expect the Daily Glucose Differential and Overnight Glucose Differential of consecutive days to be the same or similar because both compare an evening's post-prandial glucose against fasting glucose (stable). If the two values are not the same, then several conditions may be indicated:
(1) Overeating at night (to various extremes) prevented the individual's body from consistently returning to fasting glucose by morning. This is a strong indicator of potential weight gain.
(2) Other factors are interfering with overnight digestion or glucose metabolism, such as alcohol consumption, difficulties to digest food, insomnia or stress.
(3) Metabolic dysregulation is indicated (loss of stable fasting glucose)

Used together, the Daily Glucose Differential (DGD) and the Overnight Glucose Differential (OGD) are valuable metrics for assessing trends in an individual's diet and may also indicate the presence of a metabolic disorder.

Preferably, the method involves the automated generation of time and date stamps associated with the measurements. This enables the automatic calculation of the indices at the given times. Furthermore, the measurement device is enabled to calculate the duration of the overnight resting period automatically.

Furthermore, the measuring device may feature an alarm function that reminds the user to measure in the morning and in the evening. Alternately, the device could receive a wireless prompt for an external alarm device. In an ideal embodiment, the person would use the glucose measuring device as their personal alarm clock, wherein the device would prompt them to test their glucose at night when they set their wake-up alarm for the following morning; and prompt them again to test in the morning after the alarm goes off. This seamlessly integrates the measurement technique into the person's daily ritual (and does not require additional alarms or additional devices beyond what the person already requires for daily living).

Ideally, the device would be smart enough to adjust for differences in time zones (in case the person was to travel, etc.)

In another embodiment at least two glucose ranges are defined and the glucose measurements represented by the first data are classified according to in what of those ranges they fall. Subsequently, the classifications of a plurality of measurements are employed for generating the second data.

The quality of the diet can be determined according to the percentage of glucose occurring in physiologically relevant hyperglycemic ranges (low, medium, high); as well as according to the variability of the slope changes (as measured by, for example, the standard deviation of the slope).

The definition of "normal," "elevated" and "hyperglycemic" glucose levels varies among medical professionals. Glucose levels that are appropriate for the purposes of this disclosure are mentioned above. Translated into dietary guidance, meals that elevate glucose in the 70 to 125 mg/dL range are considered to have low glycemic impact. Meals that elevate glucose in the 126 to 149 mg/dL range are considered medium glycemic impact. Meals that elevate glucose above 150 mg/dL are considered to have high glycemic impact. The percentage or calculated area of measured glucose values in these three ranges can provide the basis for dietary evaluation and counseling.

The generation of the second data may involve the determination of values in phase space coordinates from the time-series of glucose measurements represented by the first data. These phase space values are further processed and/or displayed on the output device. In general, a phase space representation of a parameter reveals the dynamic properties of a system, especially if the system has some sort of periodicity (or periodicities) and if the progression of the system is followed during a time interval that is substantially larger than the periodicity one is interested in. In the case of the blood glucose level there are usually two very prominent periodicities corresponding to the time following a meal and corresponding to a day, respectively. Therefore, the analysis of the glucose progression of a plurality of days provides the user with valuable information about the stability of glucose control. However, phase space representations may as well unveil other (shorter or longer) periodicities which are important for the user's metabolism.

Suitable phase space coordinates are given by the GV measures, as well as derivatives of the GV measures. It may be useful to introduce two or more coordinates that relate to the same measure determined at different times. The phase space values may be employed for calculating a metric for GV (such as Lyapunov exponents) and/or they are displayed on the output device. Usually, from looking at phase space diagrams it is rather easy to get a qualitative picture of the stability of the progression of the observed parameter.

The time-series of glucose measurements may be selected corresponding to a time interval specified by user input. The user may select predetermined intervals such as one day or one week starting now or at a given (past or future) point in time, or the user may select an arbitrary interval, e.g. a time interval relating to the consumption of a meal and the glucose response to that meal.

Alternatively, the time-series of glucose measurements is selected corresponding to a time interval which is automatically determined based on the first data. In particular, the interval is determined corresponding to a time interval relating to a single meal, determined by detecting a rise from a glucose reference level and a return to the glucose reference level. A suitable reference level is the fasting glucose level of the subject (see above). This ensures that meaningful intervals are chosen. At the same time the operation of the disclosed system is simplified for the user. Both methods, namely defining the intervals by user input and by automatical determination may be combined within a single embodiment, such that the user is able to choose the most suitable method in any event.

Further, information, in particular information about timing, quantity and/or type of ingested foodstuffs, about physical activity and/or about values of physiological parameters such as heart rate, received from a further device or from user input is may be considered for comparing the second data with the reference data and/or for further processing the result of the comparison for generating the conclusion. This allows for carrying out meaningful comparisons and to generate precise conclusions about the nutritional quality of foodstuffs consumed by the subject and/or about a risk of long-term health complications of the subject. Furthermore, this additional information may be employed for labelling the measured and determined information if it is to be stored for later use, e. g. in a database. For example, the additional information may comprise the timing of a meal as well as the quantity and type of food consumed during that meal. After having determined the measure(s) for glycemic variability, the result may be compared to results corresponding to a number of previous meals. Due to the additional information, it is e. g. possible to detect long-term changes of the reaction to a specific meal as well as to identify foodstuffs leading to an advantageous or disadvantageous glucose response, respectively.

The measure for the glycemic variability (i.e. the second data) preferably comprises a metric for glycemic variability chosen from at least one of the following:
a) M-value;
b) Pi-index;
c) coefficient of variation;
d) J-index;
e) MODD;
f) CONGA;
g) Stability parameter;
h) Low BG index (LBGI), High BG index (HBGI) and/or CGM/BG risk index;
i) average daily risk range (ADRR).

As such, these metrics are known and scientifically tested, at least with diabetic subjects. For a detailed description of the metrics, see below. Some of the metrics have been specifically designed for analyzing spot glucose measurements. However, they may usually be employed if the CGM data is down sampled or if the metrics are adapted to CGM data. Other metrics require high measurement frequencies, i.e. usually CGM data. The different metrics have different preferred application areas; therefore it may be useful to provide a system or method that is capable of determining a plurality of these metrics. Choosing the appropriate metric depends inter alia on what question shall be answered, e.g.:
1. What is the nutritional quality of a single meal?
2. What is the daily nutritional quality of an individual's diet?
3. What is the average quality of an individual's diet during a defined time period, such as a weekend, week or month?

In the case of question no. 1, the duration of time in question (a single meal) would range from less than one hour to as much as 8 hours. To achieve sufficiently high-resolution data for this time period requires high-frequency glucose measurements, preferably CGM but possibly SMBG performed every 15 minutes. The beginning and end of the meal event are signified by the rise from and return to the individual's stable fasting glucose level. Appropriate analytical metrics include but are not limited to: CONGA, Stability Parameter, j-index and pi-index. High glycemic variability of a meal indicates the presence of high-glycemic index (fast absorbed) carbohydrates.

Question no. 2 may be answered by performing a glycemic variability analysis of a 24-hour period revealing the frequency and quantity of carbohydrates consumed during a day. Insulin resistance can also contribute to a higher and longer glycemic response. To achieve sufficiently high-resolution data for this time period requires high-frequency glucose measurements, preferably CGM but possibly SMBG performed every 30 minutes to one hour during waking hours.

The glycemic variability analysis of a longer time period, such as one week or one month, reveals the average nutritional quality of a diet, i.e. the answer to question no. 3. Insulin resistance can also contribute to a higher and longer glycemic response. CGM data is certainly favorable, but high frequency SMBG data (average 3 times per day) is also acceptable for analysis of longer time periods.

All of the mentioned metrics have their advantages and drawbacks. The Pi-index is especially worth mentioning because it involves taking into account the rise of the glucose concentration after meals which is a perfectly normal phenomenon happening in all healthy people. Because the Pi-index features the calculation of a time-dependent reference glucose value which depends on the time elapsed since the last meal, an excursion of the glucose level towards higher values happening just after a meal is taken into account differently than a similar excursion that happens at a later point in time. The task of calculating such time-dependent reference glucose values is not restricted to the Pi-index metric, however. It may as well be used in connection with other metrics. Furthermore, it is possible to not only consider the time a meal is taken but also the meal portion and/or the meal composition in order to obtain even more meaningful time-dependent reference glucose values.

The method may further comprise the steps of
a) generating third data representing a measure for a quantity of glycemic response of the subject, in particular an area-under-the-curve (AUC) value, from the time-series of glucose level measurements represented by the first data;
b) comparing the third data with a predetermined individual glycemic response budget for the qualified subject, the individual glycemic response budget representing a total amount of individual glycemic response allowable for a certain time period.

This allows for taking into account the quantity of glycemic response. As mentioned above, glycemic response is often expressed or quantified as an "area under the curve," or AUC, being calculated as the difference between measured glucose and fasting glucose. The calculated AUC value provides further information for assessing the effect of a certain event (meal, physical exercise etc.) on the organism of the subject.

There are different methods of calculating AUC values. One method termed incremental area under the blood glucose response curve (iAUC) is described in US 2005/0244910 A1 (T. M. S. Wolever et al.): The iAUC describes the area under the blood glucose response curve and above the starting (baseline) concentration, ignoring any area beneath the baseline. Therefore, as long as the offset of the measured glucose values with respect to the starting concentration is known, for calculating the iAUC a relative measurement suffices, it is not necessary to know the absolute value of the starting concentration and a calibrated measurement is not required.

The individual glycemic response budget represents a total amount of individual glycemic response allowable for a certain time period. For the given time period it may consist of a single value or of a range, e. g. setting lower and upper target levels for desired glycemic response during the established time-period. The individual glycemic response budget is may be stored in a storage of the analysis device.

The individual glycemic response budget is may be established by a healthcare professional nutritionist, based on individual attributes of the subject and/or on medical/nutritional examinations of the subject. There are two methods typically used for calculating a glycemic response budget for healthy individuals with stable fasting-glucose levels. The first method is based on Thomas Wolever and Jennie Brand-Miller's method to calculate GI for a food item, adapted to measure individual response to pure glucose as the basis for calculating an individual glycemic response budget. It includes the following steps:

1. Following a fasting period of 8 or more hours, the subject's individual fasting glucose level is measured and recorded.
2. Subsequently, the subject consumes 50 grams of pure glucose.
3. The subject's individual glycemic response is recorded as a reference curve during 2 hours, whereas a measurement is taken at least every 15 minutes.
4. Taking into account the recorded fasting glucose level the measured response is converted into an AUC quantity (for example using the trapezoidal rule, taking into account the positive difference between the measured response and the fasting glucose level), hereafter referred to as the subject's individual reference glycemic response.
5. The subject's individual carbohydrate intake allowance (for 24 hours, for example) is estimated according to age, weight, height, gender, race, BMI, nutritional goals etc. of the individual. Ideally, this calculation is performed by a doctor, a healthcare professional or a professional nutritionist.
6. The subject's individual carbohydrate intake allowance (in grams, for example) is used together with the individual reference glycemic response (see step 4) to calculate the subject's individual glycemic response budget for a defined period of time such as 24 hours. A sample calculation: a subject has an individual reference glycemic response of 100 (following the consumption of 50 grams of carbohydrates, see above, step 2) and a 24-hour recommended intake of carbohydrates of 400 grams. Therefore, the subject's 24-hour individual glycemic response budget is 800.

In the second method, the steps 1-4 of the first method are replaced by an estimation of a clinically established, average AUC value for human response to 50 g of pure glucose (adjusted for the subject's weight, gender, ethnicity, BMI, nutritional goals etc.). This reference value is assigned as the subject's individual reference glycemic response. Again, this calculation is preferably performed by a doctor, a healthcare professional or a professional nutritionist. After that, steps 5 and 6 of the first method described above follow. Further methods for calculating the individual glycemic response budget, based on individual attributes of the user and/or on medical/nutritional examinations of the user may be employed. Alternatively, the individual glycemic response budget may correspond to a prototype glycemic response representing an optimum progression of the glucose level or to a sample glycemic response that has been previously measured in the subject.

If the individual glycemic response budget is given in AUC terms as described above the calculated AUC value may be easily compared to the response budget, i.e. to a reference AUC value corresponding to a recommended total carbohydrate intake during the predetermined time-interval. However, the correlation of AUC to health and nutrition predictions may be based on further quantities such as Glycemic Index, Glycemic Load and other quantities that are known from nutritional counseling or medical research.

As mentioned above, the area under the curve is proportional to the Glycemic Load. Therefore, by calculating the AUC value a direct link to well known weight management methods is created. However, in contrast to usual methods the user does not have to rely on food labeling but he or she gets feedback corresponding to his or her actual metabolic response. Employing glycemic variability as well as glycemic response it is possible to give comprehensive information about the quantity and quality of foodstuffs as well as on the effect of food, physical activity etc. on the subject's metabolism.

Concerning the determination and processing of glycemic response values as well as concerning the comparison with a glycemic response budget, we further refer to the patent application "Method and glucose monitoring system for monitoring individual metabolic response" (EP 07 405 101.2 of 23 Mar. 2007, F. Hoffmann-La Roche AG, Roche Diagnostics GmbH), which is included by reference herein. This application discloses further advantageous features which may be used in connection with the inventive system and method.

Both approaches may be combined. For example, a result of the comparison of the third data with the predetermined individual glycemic response budget may be considered for comparing the second data with the reference data and/or for further processing the result of the comparison for generating the conclusion.

The step of providing feedback on the output device may involve user interaction in order to control interpretation, i.e. processing and output, of the second data. For this purpose, the analysis and/or output device comprises a user input device and is designed and programmed in such a way that the user may control visualization and interpretation of the second data by using the input device.

Different user interfaces and visualizations may be employed in the context of the present invention. One method for processing and displaying the second data is disclosed by the European patent application No. 06 405 457.0 (F. Hoffmann-La Roche AG) of 31 Oct. 2006. Despite the fact that the disclosed method is designed to be a visual, interactive tool for CGM data for use by people with diabetes, most of the disclosed methods may also be applied to the use with non-diabetic subjects. It involves storing a time segment of the sequence of measured glucose values and simultaneously graphically displaying a plurality of the values of the segment on a user interface display. The segments are assigned to relevant events (such as meals) and the system provides for a database for building-up a library of glucose sequences associated to different events. In particular, the user is able to record and store personally meaningful data intervals. In the context of the present disclosure these intervals can be used to calculate measures for glycemic variability relating to a single food item, meal, period of time (such as a day or week) or athletic event. Personal glycemic variability can also be used to evaluate the subject's performance with respect to dietary or health goals; and may also be used to compare similar events to gauge metabolic variability.

As an alternative to graphical display of the feedback corresponding to the result of the comparison or additionally to it, it is also possible to display numbers, in particular numbers that have a close connection to values that are relevant for weight management or nutritional counseling, such as a metric for GV compared to a target value of that metric. Furthermore, instead of displaying the feedback or additionally to it, the output may be auditory, by means of a loudspeaker or ear phones.

In particular embodiments, the measured glucose data may be saved, recalled and annotated, either in real-time or retrospectively. This allows for building up a library of reference events which e. g. facilitates comparing the current glycemic variability with the response on earlier occasions or comparing the achieved results with the individual goals. This also allows for personal notation, i. e. for keeping a personal glucose, sports and nutrition diary.

Furthermore, the disclosed method advantageously includes the step of correcting a raw signal corresponding to the measured glucose level against drift, signal instability or system error, especially if regular system calibration by blood glucose measurements is to be eliminated. For this purpose, the measuring device and/or the analysis device comprises a computer and/or an analog electronic circuit for filtering noise and/or for correcting a raw signal corresponding to the measured glucose level against drift, signal instability or system error. In principle, corresponding methods are known, see US 2005/272985 A1, EP 1 518 495 A1, US 2005/240356 A1, US 2006/052679 A1 and especially U.S. application Ser. No. 11/680,963 of 1 Mar. 2007 (all of Roche Diagnostics). According to the document cited last the method of correcting the signal includes the steps of applying a time-varying input signal to at least one of the one electrode of the sensor, monitoring a time-varying output signal produced by the sensor in response to application of the time-varying input signal, determining a complex impedance of the sensor based on the time-varying input signal and output signals, and determining from the complex impedance information relating to operation of the sensor. This information is subsequently used for determining the actual value measured by the sensor.

In the context of the disclosure a suitable measuring device is a continuous glucose monitoring device. These are computer-operated devices that can be worn, carried or implanted in or on the body for the purpose of continuous glucose measurements. Continuous glucose monitoring (CGM) devices as such are known from the field of diabetes management (they are available e. g. from DexCom, Medtronic Minimed, Abbott etc.). In principle, these known devices meet the demands on a measuring device for the present application for nutritional counseling.

One particular embodiment of the disclosure uses an implantable glucose sensor. Such a sensor is preferably coupled to the analysis device by a wireless link. Corresponding sensors are in development, e. g. by Sensors for Medicine and Science, Inc. (SMSI).

Other embodiments comprise a continuous glucose monitoring patch, to be worn on the body of the subject. Such a patch comprises a needle-type, electrochemical glucose sensor which is injected into the subcutaneous tissue. Glucose monitoring patches are very compact and lightweight, reliable and easy to use. They are commercially available, e.g. from the firm DexCom.

Alternatively, a non-invasive glucose monitoring device is employed. Furthermore, in principle most of the aspects of the disclosure may also be implemented in cases where the glucose level of the subject is measured at a sufficient rate by usual spot blood glucose measurements, e. g. by using traditional strip glucose meters.

In one embodiment of the disclosure, the measuring device (especially a CGM patch) comprises a storage for temporarily storing the first data. The first data is accumulated in the storage and off-loaded to the analysis device at a later time, in particular after the measuring device has been removed from the body of the subject. The measuring device and the analysis device comprise corresponding transmission components, such as plugs and jacks, chip readers or even wireless interfaces. It is not necessary that the data is directly transmitted from the measuring device to the analysis device but the system may be designed in such a way that the transmission of the data involves off-loading to a first device (e. g. a cellular phone, a PDA or a personal computer) and further transmission to the analysis device (e. g. via the internet or cellular data services). In this embodiment of the disclosure the measuring device constitutes a compact, lightweight stand-alone recording device for glucose data and allows for retrospective analysis as soon as the accumulated data has been transferred to the analysis device (which may be e. g. a personal computer, a specific web site, a dedicated device for analyzing glucose data or any suitable consumer electronic device). Instead of the patch, an implantable glucose sensor or a non-invasive metabolic (glucose) monitoring device having the described functionality may be employed.

Alternatively, in other embodiments the measured data is continuously submitted to the analysis device. Note that even in this case it may be advantageous to have a storage in the measuring device, especially for buffering the measured data until it has been successfully transmitted.

The first data may be transmitted to the analysis device via a wireless communication link. For that purpose, the measuring device and the analysis device comprise corresponding wireless transmission components. This allows for hassle-free and automatized communication between the measuring and the analysis devices.

In a particular embodiment, the analysis device is comprised by a handheld device which is linkable to the measuring device. Furthermore, the handheld device may comprise the analysis device as well as the output device, whereas the second data is displayed on a graphical display of the handheld device. Today's consumer electronic devices such as PDAs, cellular phones, portable digital music players etc. are capable of perform even rather complex analyses and many of them feature high resolution graphical displays. Most of these devices offer a means of wireless communication with other devices (such as Bluetooth, WLAN, IrDA etc.). These devices are easy to use, accepted by the user and inexpensive. All this makes them very appropriate for the present purpose.

Alternatively and/or additionally, a personal computer or a dedicated analysis device is employed. Furthermore, it is possible to employ combined devices comprising the measuring device, the analysis device as well as the output device, e.g. in the form of a "glucose watch".

Other embodiments and combinations of features come out from the detailed description below and the totality of the claims.

BRIEF DESCRIPTION OF THE DRAWINGS

The drawings used to explain the embodiments show.

In the figures, the same components are given the same reference symbols.

DETAILED DESCRIPTION

Figure 1A:
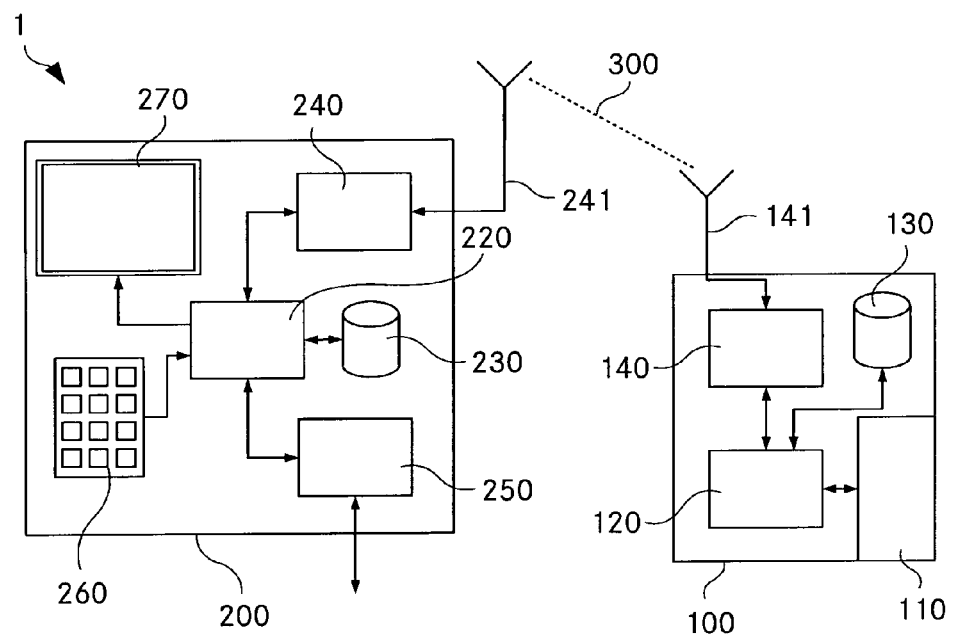
FIG. 1A A schematic representation of a system for monitoring individual metabolic response, involving monitoring of glycemic response in a qualified subject.

The FIG. 1A is a schematic representation of a system for monitoring individual metabolic response, involving monitoring of glycemic response in a qualified subject. The system 1 comprises a glucose measuring device 100 as well as a computing and display equipment 200. The two devices are linked by a wireless RF connection 300.

In the given example, the glucose measuring device 100 is to be placed on a human body and continuously measures glucose values in interstitial fluid by means of an electrochemical (alternatively: photometric) glucose sensor 110. The measuring device 100 further comprises an extra corporal part including a central processing unit (CPU) 120, a storage 130 connected to the CPU 120 and an interface unit 140. The CPU 120 controls the sensor 110 and periodically stores the blood glucose value that is actually measured in storage 130. Suitable frequencies for taking measurements are from 4 (i.e. a measurement every fifteen minutes) to 60 (i.e. a measurement every minute) measurements an hour. Periodically, the measurements stored in storage 130 are transmitted to the glucose measuring device 100 by means of the wireless RF connection 300. For this purpose, the data to be transmitted is first transmitted to the interface unit 140 by the CPU 120. The interface unit 140 pre-processes the data to be sent; this pre-processing step may include encryption of the data. Furthermore, the interface unit 140 includes a transceiver linked to an antenna 141. In one embodiment of the invention the glucose measuring device 100 comprises an arm cuff that inductively powers and communicates with a glucose sensor that is implanted in the user's arm. The arm cuff features the components of the extra corporal part and communicates with a handheld device as described in the following.

The RF signal is received by an antenna 241 of the computing and display equipment 200. This equipment further comprises an interface unit 240 connected to the antenna, including a transceiver as well as a processing stage for processing the received signals as well as signals to be transmitted (see below). The equipment 200 is controlled by a central processing unit (CPU) 220 which is connected to a storage 230, a further interface unit 250, a user input device 260 and a display 270. Controlled by the CPU 220 the received measurements may be stored in storage 230 as well as displayed on the display 270. By means of the further interface unit 250 the computing and display equipment 200 may be linked to further electronic devices such as a Personal Computer (PC) of the user or the nutritionist or further data gathering and/or storage devices such as pulsometers, pedometers, electronic scales, blood glucose meters, cellular phones, personal digital assistants (PDA) etc. This allows for automatically obtaining at least part of the meta-data (physical exercise of the user, results of individual blood glucose measurements or weight measurements, etc.) to be stored in the database.

Besides for transmitting measured values from the glucose measuring device 100 to the computing and display equipment 200 the wireless RF connection 300 also serves for transmitting control data from the equipment 200 to the measuring device 100, e.g. for changing the measurement frequency or to initiate the transmission of the data stored on the glucose measuring device 100, if the transmission is usually initiated by the equipment 200 (polling mode).

The computing and display equipment 200 may be implemented by a personal digital assistant (PDA, including portable music/multimedia players), a personal computer, a cellular or smart phone, an analyte measuring device such as a glucose measuring device, e.g. a hand held glucose meter, more preferably a strip based glucose meter, or combinations thereof. Some of these devices usually comprise most or all of the components described above: as an example, a PDA usually features wireless as well as wire-based connection interfaces (e.g. Bluetooth and USB, respectively), a rather powerful CPU, storage means (e.g. internal Flash storage and replaceable memory cards), user input devices (keys, touchpad, touchscreen etc.) as well as a display (e.g. a high resolution color LCD display). Therefore, in these cases it is sufficient to provide specific software adapted to the actual equipment 200 that provides the desired, functionality of the inventive system.

Figure 1B:
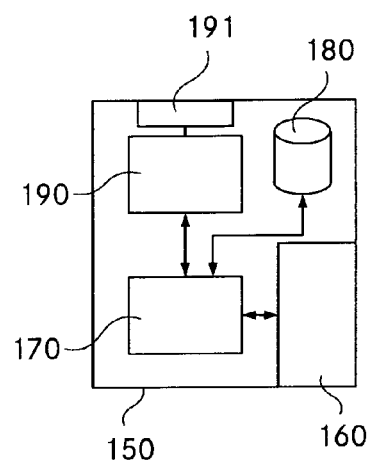
FIG. 1B a schematic representation of a continuous glucose measuring patch for another system for monitoring individual metabolic response.

The FIG. 1B is a schematic representation of a continuous glucose measuring patch 150 for another system for monitoring individual metabolic response.

The patch 150 is to be placed on a human body and continuously measures glucose values in interstitial fluid by means of a needle-type, electrochemical glucose sensor 160. The patch 150 further comprises a central processing unit (CPU) 170, a storage 180 connected to the CPU 170 and an interface unit 190 connected to a connector 191. The CPU 170 controls the sensor 160 and periodically stores the glucose value that is actually measured in storage 180 such that the measured values are accumulated. Suitable frequencies for taking measurements are from 10 (i.e. a measurement every six minutes) to 600 (i.e. a measurement every 10 seconds) measurements an hour. After the patch has been removed from the body of the user it may be connected to a further device (such as a computing and display equipment as described in connection with FIG. 1A, a personal computer or another device) by means of the connector 191. Subsequently, the measurements stored in storage 180 are transmitted to the further device. For this purpose, the data to be transmitted is first transmitted to the interface unit 190 by the CPU 170. The interface unit 190 pre-processes the data to be sent; this pre-processing step may include encryption of the data. The connector 191 can be a jack-type connector providing for a direct electrical connection or it can provide for an inductive or capacitive coupling.

Figure 2A:
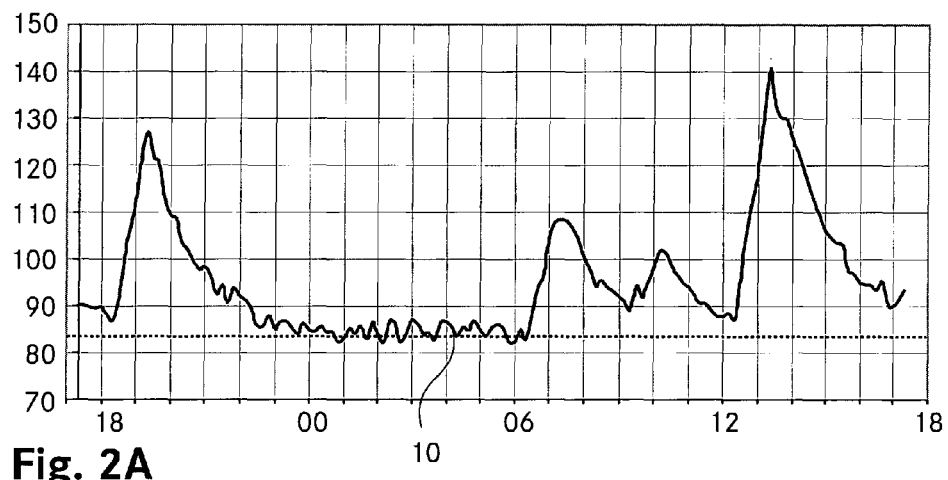
FIG. 2A, B schematic representations of two different glucose progressions measured with a measuring device of the system.
Figure 2B:
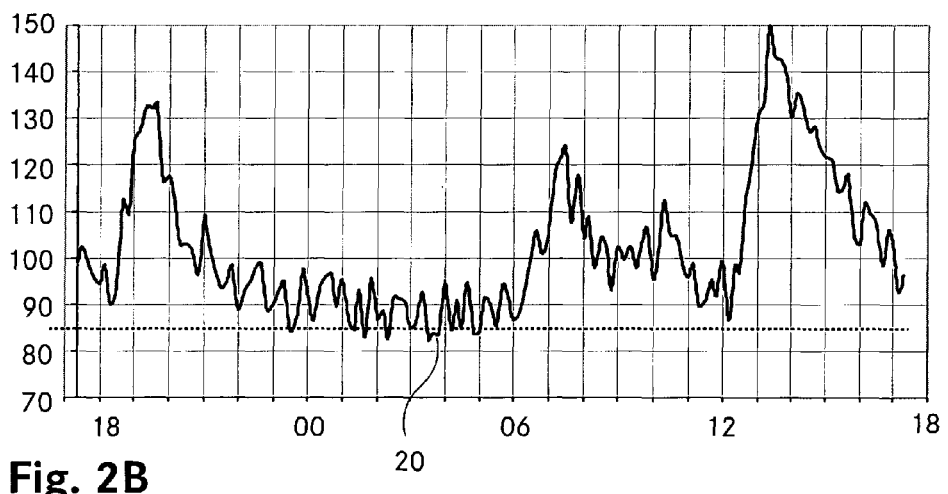

The FIGS. 2A, 2B are schematic representations of two different glucose progressions measured with a measuring device of the inventive system, in units of mg/dl. The displayed progressions represent 24 hours, starting and ending at 17:00. From the rising sections of the curves 10, 20 it is clearly visible that the users had meals around 19:00, 07:00, 10:00 and 13:00. Both curves 10, 20 represent glucose progressions that correspond to about the same value of area-under-the-curve (AUC), i.e. they relate to about the same caloric intake. However, they show different variabilities, which can already be seen qualitatively from the curves.

Figure 3A:
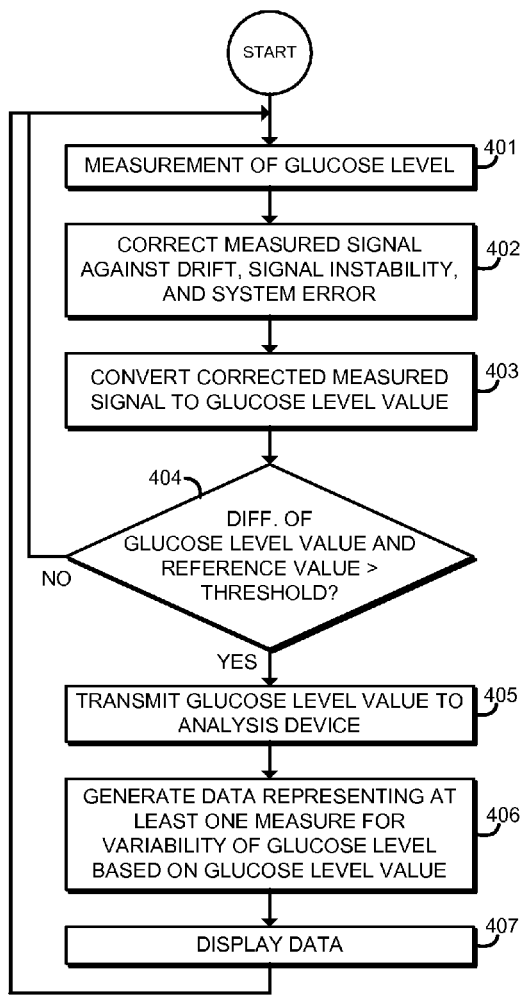
FIG. 3A, B flowcharts representing a method for monitoring individual metabolic response in real-time and involving data accumulation and off-loading.
Figure 3B:
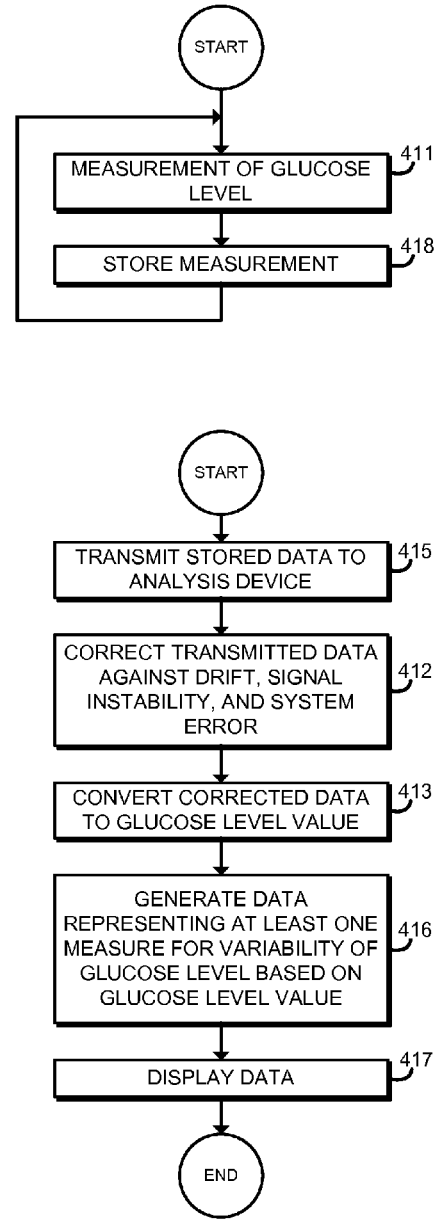

The FIGS. 3A, 3B are flowcharts representing a method for monitoring individual metabolic response in real-time and involving data accumulation and off-loading, respectively. The FIG. 3A represents the real-time process. First of all, a measurement of the glucose level is taken (step 401). The measured signal is subsequently corrected against drift, signal instability and system error (step 402), in particular according to the method as described in U.S. application Ser. No. 11/680,963 of 1 Mar. 2007 (Roche Diagnostics). The resulting corrected signal is converted to a glucose level value (e. g. in mg/dl) (step 403). In a next step 404 the actually measured glucose level value is compared to a reference value corresponding to the previously measured value. If the difference of the two values does not exceed a certain minimum threshold (such as e. g. 3 mg/dl) no further action is taken and the process continues with taking another measurement (step 401) after a predetermined time.

Only if the minimum threshold is exceeded the actual glucose level value is transmitted to an analysis device (step 405). For the event of very long stable intervals, the process may involve the transmission of the value even if the difference does not exceed the minimum threshold, provided that a certain minimum interval has elapsed since the last transmission (e.g. 1 hour). This ensures that failures of the glucose measuring device inhibiting the transmission of measured values to the analysis device are not mistaken for stable glucose progressions.

In the analysis device the transmitted glucose level value is used to generate data representing at least one measure for variability of the glucose level of the subject, in particular according to one of the methods described below (step 406).

Finally, the updated data is displayed on a display device (step 407). The process (steps 401-407) is repeated in a cycle in order to ensure constant updates of the displayed information. The displaying step 407 may involve user interaction in order to control the display of the data, to update or modify a database of metabolic response data, to control the operation of the device etc. (see below).

The FIG. 3B represents the retrospective process. In a continuous glucose measuring patch as described in connection with FIG. 1B above, a measurement of the glucose level is taken (step 411). The measurement is subsequently stored in a storage of the patch (step 418). These steps are repeated as long as the patch is placed on the body of the user.

After the patch has been removed from the body the accumulated data stored in the storage is transmitted to an analysis device (step 415). Using further data stored on the storage of the patch the transmitted data is corrected against sensor drift, signal instability and system error (step 412), in particular according to the method as described in U.S. application Ser. No. 11/680,963 of 1 Mar. 2007 (Roche Diagnostics). The resulting corrected signal is converted to a glucose level value (e.g. in mg/dl) (step 413). This value is used to generate data representing at least one measure for variability of the glucose level of the subject, in particular according to one of the methods described below (step 416). Finally, the data corresponding to the event is displayed on a display device (step 417). Again this last step may involve user interaction.

The patch may be placed on the body again to collect further data.

The illustrative system allows for calculating measures for glycemic variability which are indicative of the user's state of health. The measures are calculated within the computing and display device 200 and may be displayed in number or graphical form on the display 270. In the following, some suitable measures (metrics) for glycemic variability are presented. Detailed information about how these measures may be calculated from the measured glucose values can be found in the referenced documents. It is to be noted that the calculation of the measures may be based directly on the measured glucose value but also on derived quantities, such as e. g. the offset of the glucose value against a reference value (e. g. the fasting glucose level) or a glucose progression that has been smoothed in order to eliminate fluctuations caused by the measuring device.

A metric that has long been known is denoted M-value (Schlichtkrull J, Munck O, Jersild M: The M-value, an index of blood sugar control in diabetes mellitus. Arch Med Scand 1965; 177:95-102). It involves calculating the following measure:

$$M_{GR} = \frac{\sum_{t=t_1}^{t_k} \left|10 \times \log \frac{GR_t}{IGV}\right|^3}{k},$$

where k denotes the number of measurements, $GR_t$ denotes the glucose value measured at time t and IGV denotes a pre-determined "ideal" glucose value. Due to employing the absolute value of a logarithm, the measure depends on the variation of the glucose value, in contrast to a simple mean of glucose values. An M-value of 0 corresponds to optimum glucose control. In principle, the M-value is a suitable measure within the context of the present invention, providing a simple parameter being representative of the glucose variations. However, the M-value relies on the selection of an arbitrary glycemic reference point, which introduces ambiguities and possible bias effects. Furthermore, due to the structure of the formula, hypoglycaemia has a greater impact on the M-value than hyperglycaemia, which limits the M-value's usefulness as a true descriptor of glycemic variation.

The following M-values are calculated for the examples displayed in FIGS. 2A, 2B depending on different values of the "ideal glucose value" IGV:

| IGV | M-value FIG. 2A | M-value FIG. 2B |
|---|---|---|
| 85 (fasting) | 0.69 | 1.42 |
| 90 | 0.39 | 0.86 |
| 95 | 0.26 | 0.52 |
| 100 (~mean glucose) | 0.26 | 0.36 |

Another, in most situations more suitable metric is denoted π-index ("pi-index", see B. M. Pfeiffer et al., "A Mathematical Index of Short Term Courses of Continuous Glucose Traces", Institute for Diabetes-Technology, Ulm, Germany). It is based on a distinction between glucose values that are within a physiological range and values that are below or above that range. The lower bound of the physiological range is constantly set to 50 mg/dl, whereas the higher bound is time-dependent: At the beginning of a meal it is set to 200 mg/dl, it linearly falls to 180 mg/dl during the first two hours after the meal and further falls linearly to 110 mg/dl during the subsequent six hours. A (variable) midpoint value is defined as the geometric mean of the lower and the higher bound at a given point in time.

For every glucose measurement the deviation from the midpoint is calculated according to the M-value formula (see above). From these deviations the π-value as well as the π-ratio may be calculated as explained in detail in the referenced document. During this calculation, deviations corresponding to glucose values lying outside the physiological range are differently treated from deviations that lie within the physiological range. The π-value is a deviation measure of the glucose trace with respect to the midpoint glucose target, whereas the π-ratio is a measure of the relation of glucose values above and below the midpoint. Low π-values indicate good glucose control with rather small deviations from an optimum glucose progression, whereas high π-values are an indication of possibly unhealthy food choices leading to large variations of the glucose level. The π-ratio allows for assessing whether the individual tends to experience hypoglycemias (π-ratio below 1) or hyperglycemias (π-ratio above 1). In the context of the disclosure, the π-value provides an easy-to-understand parameter reflecting the metabolic effect of the food choices of the user. In order to optimize his or her diet the user may simply strive for reducing the π-value below a given target value.

Initially, the π-value/π-ratio metric has been developed for the application with diabetic subjects. In order to adapt the method to healthy subjects it may be useful to modify the method, e.g. by changing the boundary values of the physiological range to values adapted to healthy persons or by omitting the distinction between physiological/non-physiological values, thereby just modifying the M-value approach by introducing varying "ideal" glucose values. The π-value/π-ratio metric is open to further generalization, e.g. by modifying the progression of the higher bound of the physiological range or by introducing a variable lower bound. Furthermore, the midpoint may be calculated from the bounds and/or from the time since the last meal in a different way.

If the distinction between physiological/non-physiological values is omitted, π-values of 0.21 and 0.60 are calculated for the curves 10, 20 displayed in FIGS. 2A, 2B as well as π-ratios of 0.83 and 0.63, respectively.

A very simple metric is given by the so-called Coefficient of Variation (CV, see David Rodbard, "Optimizing Display, Analysis, Interpretation and Utility of Self-Monitoring of Blood Glucose (SMBG) Data for Management of Patients with Diabetes." Journal of Diabetes Science and Technology, Volume 1, Issue 1, January 2007. Page 66). It is defined as

% CV=100×SD/MBG, where MBG denotes the mean glucose level and SD denotes the standard deviation of the glucose level. The curves 10, 20 displayed in FIGS. 2A, 2B yield CVs of 13.2 and 14.6, respectively.

A further, very simple metric is given by the so-called J-index (Wojcicki J M: "J" index. A new proposition of the assessment of current glucose control in diabetic patients.", Horm Metab Res 1995; 27:41-42). It is defined as follows:

$$J=0.324\times(MBG+SD)^2,$$

where MBG denotes the mean glucose level and SD denotes the standard deviation of the glucose level (each measured in mmol/l). It incorporates the mean level as well as the variability of the glucose level into one measure. The values of the J-index for the curves 10, 20 displayed in FIGS. 2A, 2B amount to 11.7 and 13.7, respectively.

A suitable metric for longer-term glycemic variation is given by the so-called MODD (mean of daily differences, see Molnar G D, Taylor W F, Ho M M: Day to day variation of continuously monitored glycaemia: A further measure of diabetic instability. Diabetologia 1972; 8:342-348), defined as $$MODD = \frac{\sum_{t=t_1}^{t_{k^*}} |GR_t - GR_{t-1440}|}{k^*},$$

where k* denotes the number of observations that are taken into account, whereas each two subsequent observations are performed at an interval of 24 hours; $GR_t$ denotes the glucose value measured at time t, $GR_{t-1440}$ denotes the glucose value measured 24 hours earlier. A MODD value of less than 1.0 indicates that the individual has low GV (or highly reproducible GV). A high MODD value indicates high variability in the glucose signal over time. However, a high value can be the result of a metabolic dysfunction but also of irregular habits of the monitored individual.

In contrast to MODD the CONGA metric (continuous overlapping net glycemic action, see C. M. McDonnell, et al. "A Novel Approach to Continuous Glucose Analysis Utilizing Glycemic Variation," Diabetes Technology and Therapeutics, Vol. 7, No. 2, 2005, 255) is appropriate for assessing intra-day glycemic variation. For each observation after the first n hours of observations, the difference between the current observation and the observation n hours previous is calculated. CONGAn is defined as the standard deviation of the differences:

$$CONGAn = \sqrt{\frac{\sum_{t=t_1}^{t_{k^*}}(D_t - \overline{D})^2}{k^* - 1}},$$

where k* denotes the number of glucose measurements taken into account, $D_t$ denotes the difference between the glucose value measured at time t and the glucose value measured n hours earlier (in mmol/l) and $\overline{D}$ denotes the mean value of all measured values of $D_t$. Higher CONGA values therefore indicate greater glycemic variation. CONGA does not require the presetting of arbitrary cut-offs or target values and its significance is widely independent of whether the user has constant rather habits or not. For the curves 10, 20 displayed in FIGS. 2A, 2B the following values are obtained for n=1, 2, 4:

| n | CONGAn FIG. 2A | CONGAn FIG. 2B |
|---|---|---|
| 1 | 0.74 | 0.86 |
| 2 | 0.98 | 1.09 |
| 4 | 0.96 | 1.12 |

Another way of generating parameters that represent the fluctuations of a measurement series obtained by continuous glucose monitoring involves analyzing a series of measuring data that are correlated to the concentration of glucose for a number of time points that are distributed over a period of at least 8 hours. Multiple time intervals, each extending over at least one hour, are selected from that period of time. Subsequently, a stability parameter is determined for each of the time intervals by analyzing measuring data of the corresponding time interval. By analyzing the stability parameters it is possible to determine disease-related particularities of the metabolism. One of the advantages of that method lies in the fact that the need for calibration of the measuring device is reduced or even eliminated.

For calculating the stability parameter for a given time interval the values measured during that interval are transformed by a linear transformation in a first step. The linear transformation is chosen such that the mean of the transformed values corresponds to a preset value, e.g. 0, and that the standard deviation of the transformed values corresponds to another preset value, e.g. 1. In a second step, the first time derivative of the transformed measuring data is formed by well-known numerical techniques. The stability parameter is then given by the standard deviation of this time derivative. In a healthy subject, food intake-related increases in the glucose concentration are rapidly counteracted. Therefore, the standard deviation of the time derivative of the glucose level is relatively large, and both large positive and large negative values of the first time derivative are present in a comparably short time interval. If the glucose metabolism is disturbed, large positive values of the time derivative occur but not large negative ones. These differences (and other aspects) may be recognized by studying the stability parameter(s). In the context of the invention, a number of optimum stability parameter values (or ranges) may be compared to the values actually determined from the glucose measurements. Differences may indicate potential for optimization.

Another simple metric for glycemic variability is given by the standard deviation of the slope. The slope may be calculated from a functional fit to the measured glucose values or, more simply, by investigating the differences between subsequent measurements, taking into account the temporal separation between these measurements. Using the second method one obtains 0.35 for the standard deviation of the slope of the curve 10 displayed in FIG. 2A (using units of mg/dl) and 0.71 for the standard deviation of the slope of the curve 20 displayed in FIG. 2B, respectively.

Other metrics called Low BG Index (LBGI) and High BG Index (HBGI) provide risk indices of low and high BG events over time (see e.g. B. Kovatchev et al., "Algorithmic Evaluation of Metabolic Control and Risk of Severe Hypoglycaemia in Type 1 and Type 2 Diabetes Using Self-Monitoring Blood Glucose Data," Diabetes Technology and Therapeutics, Volume 5, Number 5, 2003. pp. 817-828). To calculate these metrics the following three steps are performed:

1. Firstly, a nonlinear transformation is applied to the BG measurement scale to map the entire BG range (20-600 mg/dl) to a symmetric interval ($-\sqrt{10}, \sqrt{10}$). The point 112.5 mg/dL, which is the clinical center of the BG scale, is mapped to 0. If the glucose level is measured in mg/dL the analytical form of this transformation is $$f(BG) = 1.509 \times [(\ln(BG))^{1.084} - 5.381]$$

(see B. Kovatchev et al., "Symmetrization of the Blood Glucose Measurement Scale and its Applications", Diabetes Care, Volume 20(11). November 1997.1655-1658).

2. Next, a risk value is assigned to each glucose value. The quadratic risk function is defined as follows:

$$r(BG) = 10 \times f(BG)^2.$$

It ranges from 0 to 100. Its minimum value is achieved at BG=112.5 mg/dl, while its maximum is reached at the ends of the BG scale.

3. Finally, the metrics LBGI and HBGI are calculated as follows:

$$LBGI = \frac{1}{n}\sum_{i=1}^{n} rl(x_i),$$

$$HBGI = \frac{1}{n}\sum_{i=1}^{n} rh(x_i),$$

where rl(BG)=r(BG) if f(BG)<0 and 0 otherwise and rh(BG)=r(BG) if f(BG)>0 and 0 otherwise. LBGI increases when the number and/or extent of low BG readings increases. Therefore, LBGI is an indicator of the risk for hypoglycaemia. HBGI increases when the number and/or extent of high BG readings increases. Therefore, HBGI is an indicator of the risk for hyperglycaemia.

The following values are obtained for the glucose progressions displayed in FIGS. 2A, 2B:

| metric | FIG. 2A | FIG. 2B |
|---|---|---|
| LBGI | 1.48 | 0.90 |
| HBGI | 0.05 | 0.14 |

According to the publication of Kovatchev et al. mentioned above, an LBGI value of 1.48 corresponds to a low risk for hypoglycemia, whereas a value of 0.90 corresponds to a minimal risk for hypoglycemia. However, the publication relates to diabetic people. For healthy people it may be sensible to provide higher limits for LBGI as well as lower limits of HBGI.

Another metric for glycemic variability is denoted ADRR (average daily risk range). It has been developed by B. Kovatchev et al. for processing routine self-monitored blood glucose (SMBG) data (B. Kovatchev et al., "Evaluation of a New Measure of Blood Glucose Variability in Diabetes", Diabetes Care, Volume 29, Number 11, November 2006, 2433). The ADRR is computed from 2-4 weeks of SMBG data with a frequency of at least 3 readings a day; it is sufficient to have 14 days with at least 3 readings a day over one month. First, the glucose measurements are transformed by the mapping as known from the LBGI/HBGI measures (steps 1 and 2 as discussed above).

Finally, the metric ADDR is calculated as follows:

$$ADDR = \frac{1}{M}\sum_{i=1}^{M}[LR^i + HR^i],$$

where $LR^i = \max[rl(x_1^i), \ldots, rl(x_n^i)]$ and $HR^i = \max[rh(x_1^i), \ldots, rh(x_n^i)]$ for day i; i=1, 2, . . . , M. Again, rl(BG)=r(BG) if f(BG)<0 and 0 otherwise and rh(BG)=r(BG) if f(BG)>0 and 0 otherwise.

Low values of ADDR (less than 20 for diabetic patients) indicate a low risk for hypo- and hyperglycemia; higher values indicate higher risks.

Figure 4A:
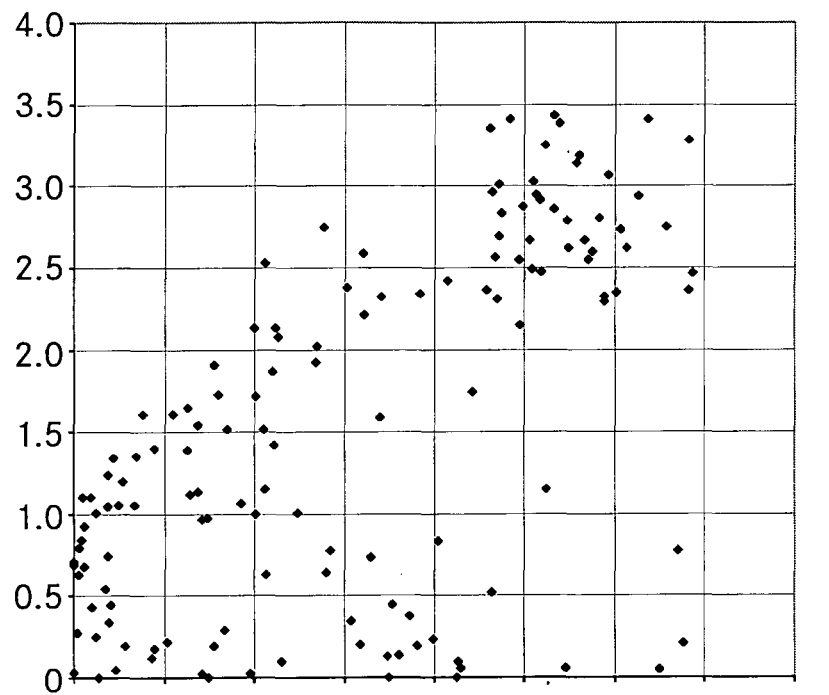
FIGS. 4A, B phase space diagrams of the BG risk index calculated from the glucose progressions displayed in FIGS. 2A, 2B.
Figure 4B:
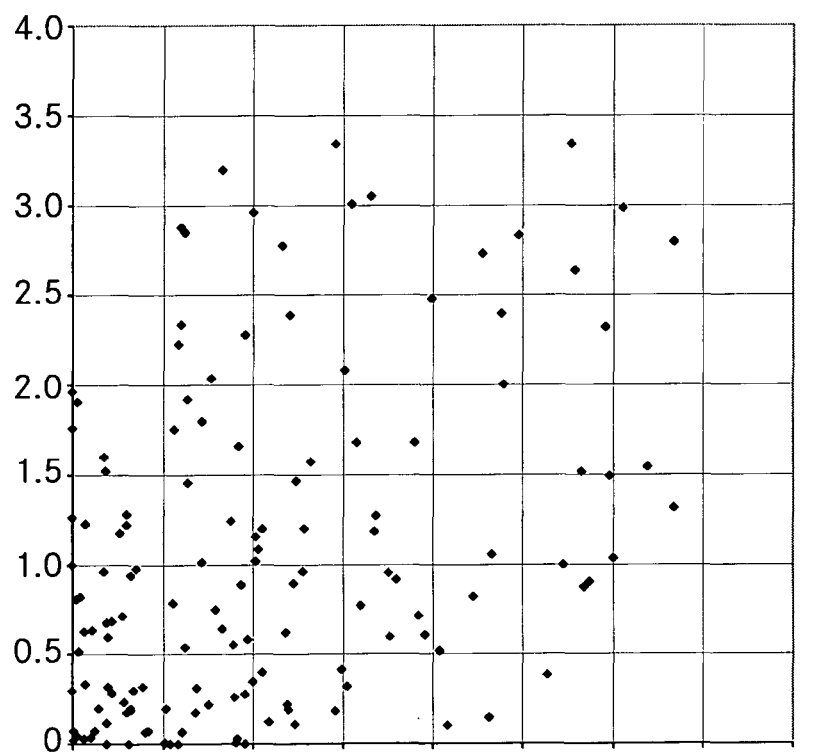

Based on the LBGI/HBGI indices another index called BG Risk Index may be calculated, being a measure for the overall risk of extreme blood glucose. The BG Risk Index is simply defined as being the sum of LBGI and HBGI (see B. Kovatchev et al., "Quantifying Temporal Glucose Variability in Diabetes via Continuous Glucose Monitoring: Mathematical Methods and Clinical Application," Diabetes Technology and Therapeutics, Volume 7, Number 6, 2005. PP. 849-862). In the examples shown in FIGS. 2A, 2B the BG risk index amounts therefore to 1.53 and 1.04, respectively. It is suggested to visualize the BG Risk Index over time in the form of a phase space diagram, plotting the BG Risk index at time t against the BG Risk index at time t−1 hour. A smaller, more concentrated attractor indicates system stability; a more scattered diagram indicates system irregularity and reflects poor glucose control. The results for the BG Risk Index obtained from the curves 10, 20 displayed in FIGS. 2A, 2B are displayed in FIGS. 4A, 4B. It is clearly visible that the attractor is more concentrated in FIG. 4A, indicating better glucose control.

Figure 5A:
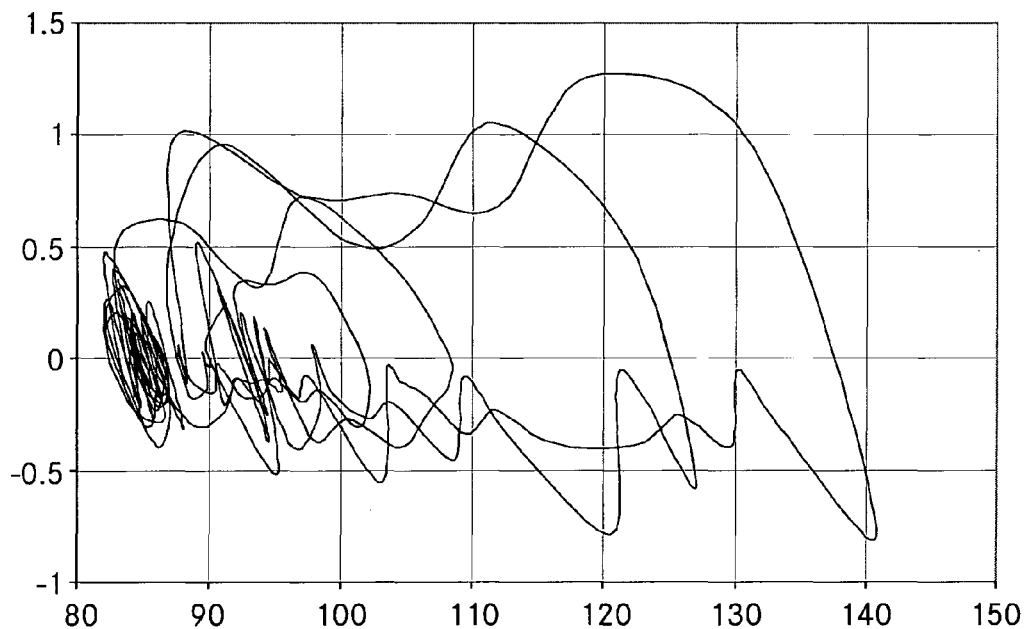
FIGS. 5A, B phase space diagrams representing the glucose values as well as the first derivative of the glucose progressions displayed in FIGS. 2A, 2B.
Figure 5B:
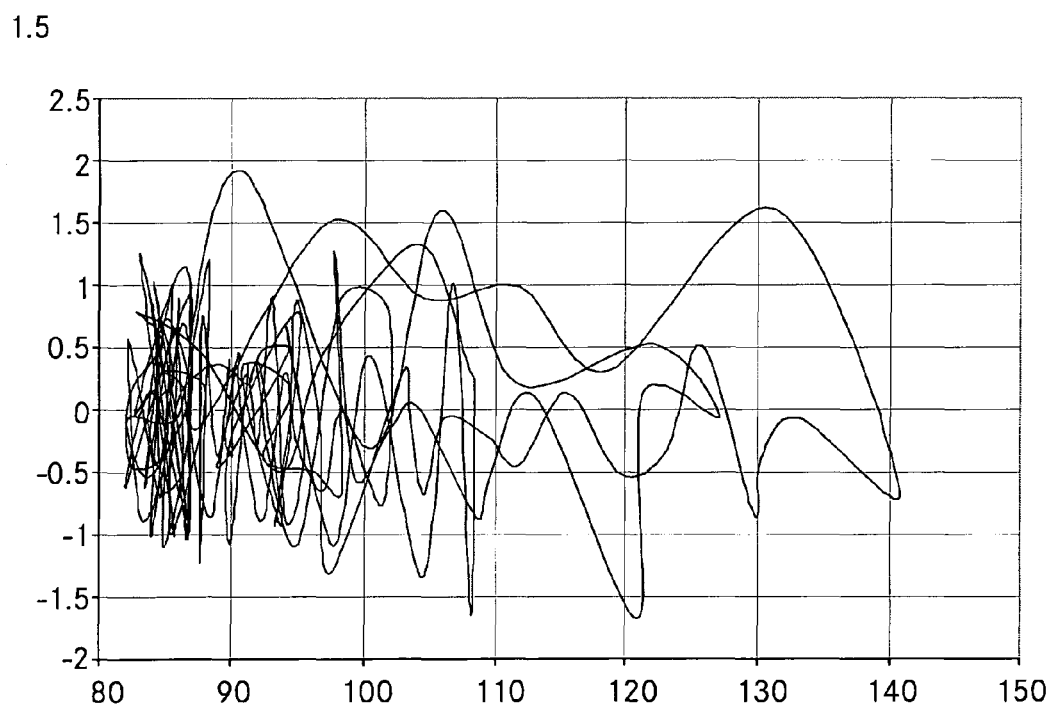

The plot of the BG Risk Index mentioned before is an example for a phase space representation of measured values. There exist further phase space methods that are suitable for the analysis of the variability of glucose progressions. In general, a phase space representation reveals the dynamic properties of a system. The FIGS. 5A, 5B show simple phase space diagrams representing the measured glucose values on the horizontal axis in mg/dl versus the rate of change of the glucose level in mg/(dl min) on the vertical axis, for the curves 10, 20 as displayed in FIGS. 2A, 2B, respectively. It is clearly visible that the attractor of the representation in FIG. 5A is much more stable than the one in FIG. 5B. This is another indication for better glucose control. These phase space diagrams may be further analyzed by known mathematical methods. For example, long-term signal dynamics may be analyzed by means of global Lyapunov exponents, short-term signal dynamics may be analyzed by means of local Lyapunov exponents.

Instead of just displaying the glucose level as well as its derivative, it is possible to use more advanced parameters; furthermore it is possible to employ more than two dimensions for the phase space. For further detail see EP 1 702 559 A2 (Roche Diagnostics, F. Hoffmann-La Roche AG).

Further metrics for glycemic variation exist (cf. e.g. C. M. McDonnell, et al. "A Novel Approach to Continuous Glucose Analysis Utilizing Glycemic Variation," Diabetes Technology and Therapeutics, Vol. 7, No. 2, 2005. Page 255) or may be devised, in particular methods that involve calculating first and/or higher derivatives of the glucose progression.

The values and/or progressing of the values obtained from the metrics described above (or other kinds of metric) are further compared with reference data such as target values or ranges. Short-term metrics allow for drawing conclusions about the quality of a meal or about the effects of physical exercise. Long-term metrics allow for drawing a conclusion on whether the user's glucose control is good or whether the user should go about changing his or her eating habits or do more (or less) physical exercise. The conclusions may be displayed by simple graphical symbols (such as smilies, ranges with an indicator needle, colour codes etc.), by more complicated graphical diagrams, such as curves, or by text output. These means of displaying information may be combined with each other. Instead of or additionally to visual display the feedback may be given otherwise, especially auditorily.

Additionally to the glycemic variability information, the system may provide the possibility of calculating the area under the curve (AUC) accumulated during a certain time interval. Furthermore, the system may include the possibility of doing comparisons between the calculated AUC and a predetermined glycemic response budget for the user. These functionalities are more closely described in the European patent application "Method and glucose monitoring system for monitoring individual metabolic response" (EP 07 405 101.2 of 23 Mar. 2007, F. Hoffmann-La Roche AG, Roche Diagnostics GmbH).

Figure 6:
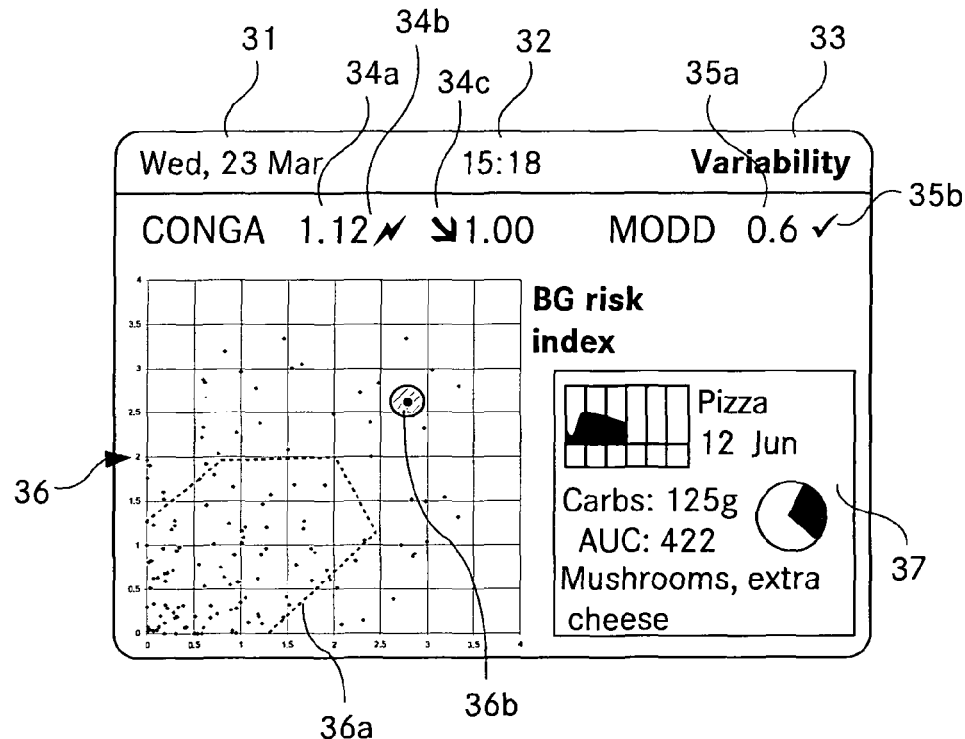
FIG. 6 the graphical user interface for displaying information on glycemic variability.

The FIG. 6 shows the graphical user interface for displaying information about glycemic variability. The graphical user interface (GUI) may be displayed on the computing and display equipment. In the displayed mode, the following information is provided:
a) the current date 31;
b) the current time 32;
c) an indication 33 of the current display mode ("Variability");
d) the value 34a of the CONGA metric (see above) for intra-day glycemic variability together with an indicator 34b about the quality of the value 34a compared to a reference value and (if the CONGA metric is not within the optimum limits) a target value 34c for the CONGA metric;
e) the value 35a of the MODD metric (see above) for inter-day glycemic variability together with an indicator 35b about the quality of the value 35a;
f) a phase space plot 36 of the BG risk index (as displayed in FIGS. 4A, 4B), the horizontal axis denotes the BG risk index at a time t, the vertical axis denotes the BG risk index at a time t−1 hour.

In the phase space plot 36 a target region is marked by a boundary line 36a. Using the graphical interface, the user may move a marker 36b to select one of the points of the plot, e.g. by touching it (if the GUI is displayed on a touch screen) or by using some other input means. Subsequently, further information about the selected measurement is displayed, e.g. the date and time of the measurement as well as the corresponding glucose value. If stored in the internal database, further information 37 about a corresponding event (e.g. a preceding meal) together with a shape representation of the glucose progression and results of the glycemic budget calculation are displayed.

The described graphical user interface offers a wealth of information and may be suitable for very experienced users who want to most efficiently tune their diet (such as e.g. athletes) or for nutritional counsel. Simpler user interfaces may be provided for general users, e.g. interfaces that focus on one variability metric at a time and that visualize the metric simply by displaying the result of a comparison with a target value, i.e. by indicating whether the GV metric is "good", "average" or "poor" or by displaying an indicator needle pointing to a "green", "yellow" or "red" region of a scale.

Figure 7:
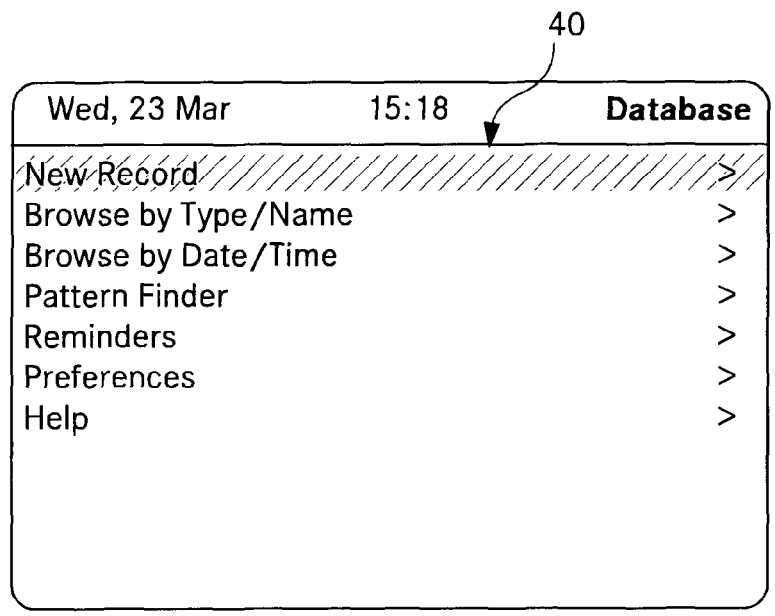
FIG. 7 the archive menu of the graphical user interface, displayed on computing and display equipment.

The FIG. 7 shows the database menu of the graphical user interface, displayed on a computing and display equipment. In the given example, the graphical user interface resembles the Apple-Ipod interface. Correspondingly, choosing from menu options or adjusting parameters can be effected using a click wheel. However, other input means such as a touch screen, a touch pad or conventional keys and/or other user interfaces (such as user interfaces provided by the operating systems Microsoft Windows, Linux, MacOS, Symbian, or others) are appropriate as well. The corresponding menu structure may be realized on other equipment such as PDAs, mobile/smart phones etc.

Figure 8:
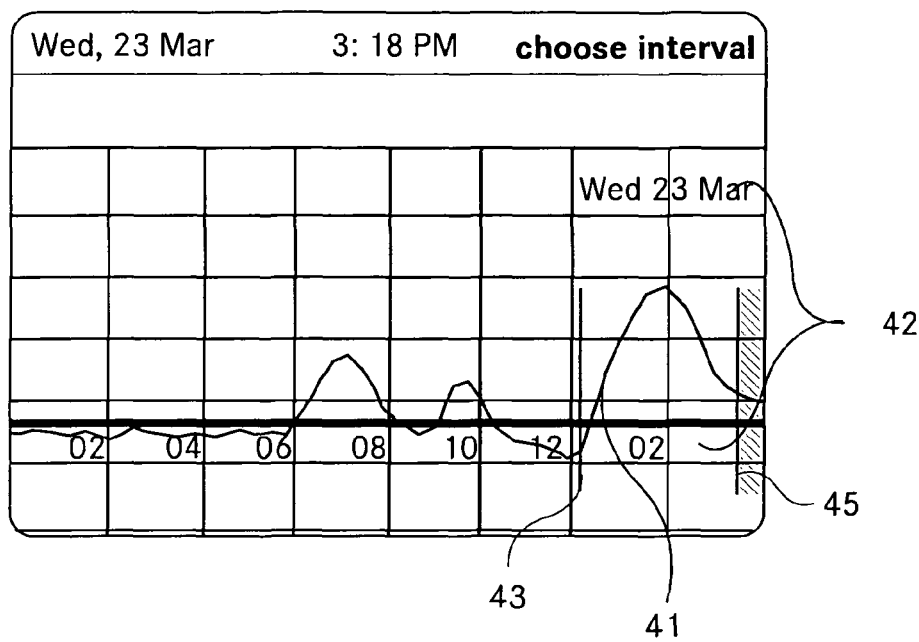
FIG. 8 the graphical user interface for choosing a time interval from pre-recorded data.

The menu 40 shown in FIG. 7 allows for choosing from the following options:
a) New Record
b) Browse by Type/Name
c) Browse by Date/Time
d) Pattern Finder
e) Reminders
f) Preferences
g) Help A new record may be generated by choosing option a). Each record will be linked to an "event" such as a meal, a certain sequence of physical exercise or a time period such as a day or week. FIG. 8 shows an option for defining the time interval in which the measured glucose values will contribute to the recorded response.

In the course of generating a new record, the user will be prompted for a name. The name should be a short but meaningful description of the corresponding event (e.g. "Pizza" or even "Pizza for lunch") or time interval (e.g. "Monday 12 Jun") and will serve as a kind of "file name". It is one of the prime identifiers of the event (besides further meta-data such as time and date, food portion size etc., see below). Further meta-data may be gathered by querying the user or from external devices such as pulsometers, pedometers, cellular phones, personal digital assistants (PDA) etc. or personal computers and automatically be stored in the database.

By choosing options b) and c) from the database menu as shown in FIG. 7 records stored earlier in the database may be retrieved, employing different criteria. The shapes may be browsed by type and name (see FIG. 9, comment below) or by date and time.

Option d) allows for finding patterns, i.e. earlier records that match a certain AUC shape or that have shown similar behavior of glycemic variability metrics. Option e) allows for defining, editing and deleting reminders. These reminders may be triggered by a number of events: the lapse of a certain time period (count down), a certain point in time, reaching a certain glucose level or predefined events regarding the glucose level or a measure for glycemic variability (passing of a maximum/minimum, exceed a BG gradient etc.) The reminders may have a mere warning function or they may be displayed in combination with a prompt that invites the user to provide information or that proposes certain actions (as starting to record measurements for generating a new shape). By choosing option f) certain user preferences (display brightness and contrast, colors, screen saver, graph options, measuring options etc.) may be edited. Finally, option g) displays a help menu, providing access to various documentation about using the software.

Each record stored in the database corresponds to a certain time interval. These intervals may be automatically assigned by the disclosed device, or they may be defined by the user. The interval may be defined beforehand, during the interval or even after it has ended. FIG. 8 shows a suitable graphical interface for defining an interval that has already ended. The measurements received from the measuring device are continuously stored in the storage of the computing and display equipment, in such a way that the progression of the glucose level during a certain time span (e. g. 16 hours) before the actual time is always available. The progression of the glucose level is displayed as a curve 41, together with time and date information 42 ("Wed 23 Mar", "14 16 18 . . . 02"). By shifting a start bar 43 as well as and end bar 45 the time interval in which the measured glucose values shall contribute to a new record may be defined by the user. In order to obtain standardized shapes consisting of 1-hour segments the chosen interval is extended to the next full hour. The maximum recording time is limited to 6 hours, in order to ensure adherence to the event context.

After the user has defined the time interval a new record is automatically generated. Subsequently, the user may amend the new instance with further information, such as a title and a description. Finally, the record is stored in an event type directory (see above and FIG. 9).

The time span during which the progression of the physiological parameter is still available and accessible by the user is deliberately chosen to be limited to about 1-2 days, in order to ensure that the information supplied by the user relating to the time span and the corresponding event (food intake, physical activity etc.) is as correct as possible. In principle, it is possible to store information on the device that relates to longer time spans, however this information should not be eligible for generating new instances and records. It could however be valuable for the patient's HCP.

Alternatively to the user-defined time interval, the interval may be automatically determined based on the first data. If e.g. the interval is to correspond to a time interval relating to a single meal, it is determined by detecting a rise from a glucose reference level and a return to the glucose reference level, such as the fasting glucose level of the subject.

Figure 9:
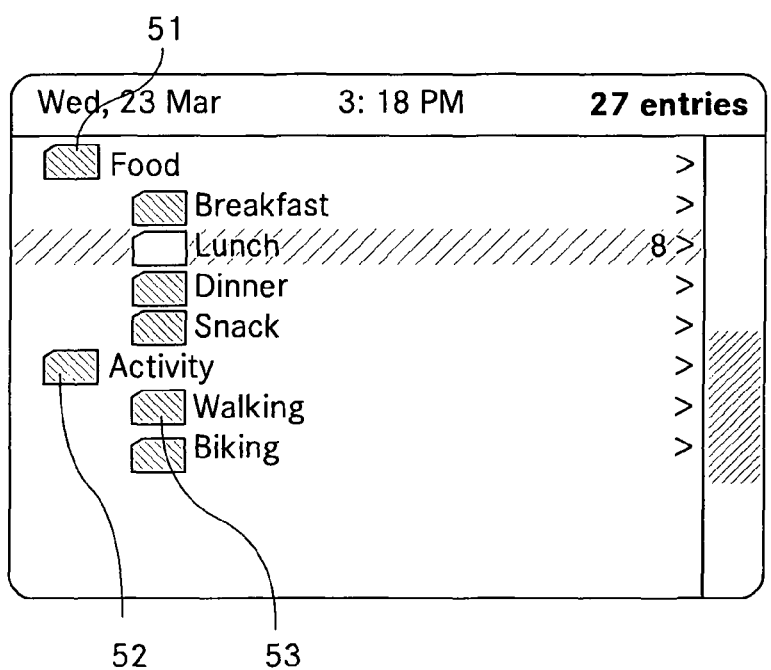
FIG. 9 the directory structure for storing and retrieving archived responses into and from the database, respectively.

FIG. 9 shows the directory structure for storing and retrieving records into and from the database, respectively, where the shapes are hierarchically grouped by event type. On a first (top) level the events are divided into two groups ("Food", "Activity") containing events 51 that are related to ingestion and events 52 that are related to physical activity. On a second level, the events are further classified into specified event types 53 that relate to specific contexts (such as in the given example breakfast, lunch, dinner, snack for ingestion events, as well as walking, biking for physical activity events). The user is free to create further, custom event types and/or groups.

Figure 10:
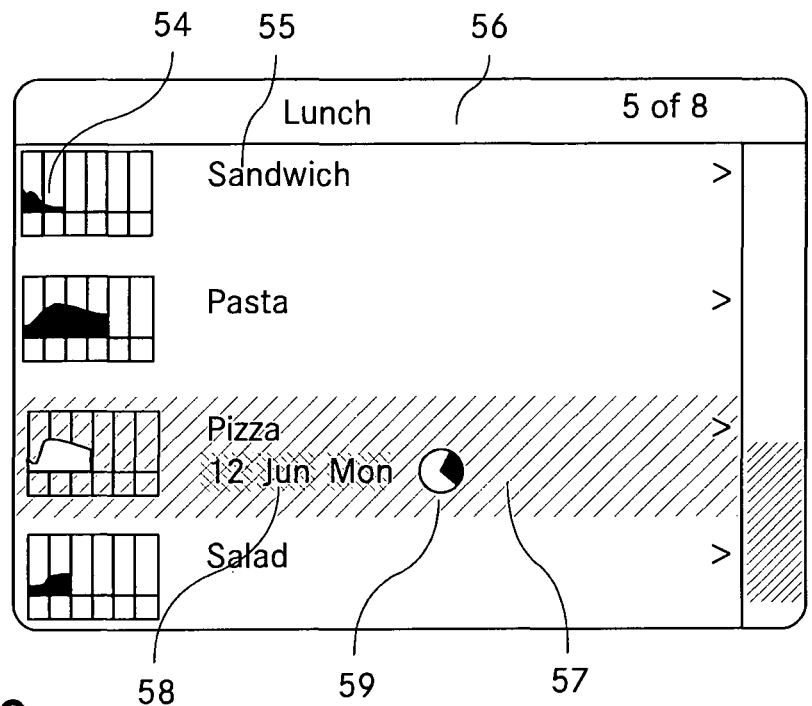
FIG. 10 the thumbnail representation of a response within a given directory.

Once a given event type directory is chosen, the contained records ("Sandwich, Pasta, Pizza, Salad") are displayed, as is shown in FIG. 10. This includes the display of a thumbnail representation 54 of every event within the given directory as well as of the names 55 assigned to all the displayed records. The title bar 56 shows the name of the directory that corresponds to the name of the event type ("Lunch"). For the record 57 that is currently highlighted additionally the date and weekday 58 ("12 Jun Mon") as well as the time and interval 59 of the latest recorded incident are displayed. The time and interval information 59 is given as a marked segment of a clock face. This allows for quickly identifying the relevant information.

Figure 11:
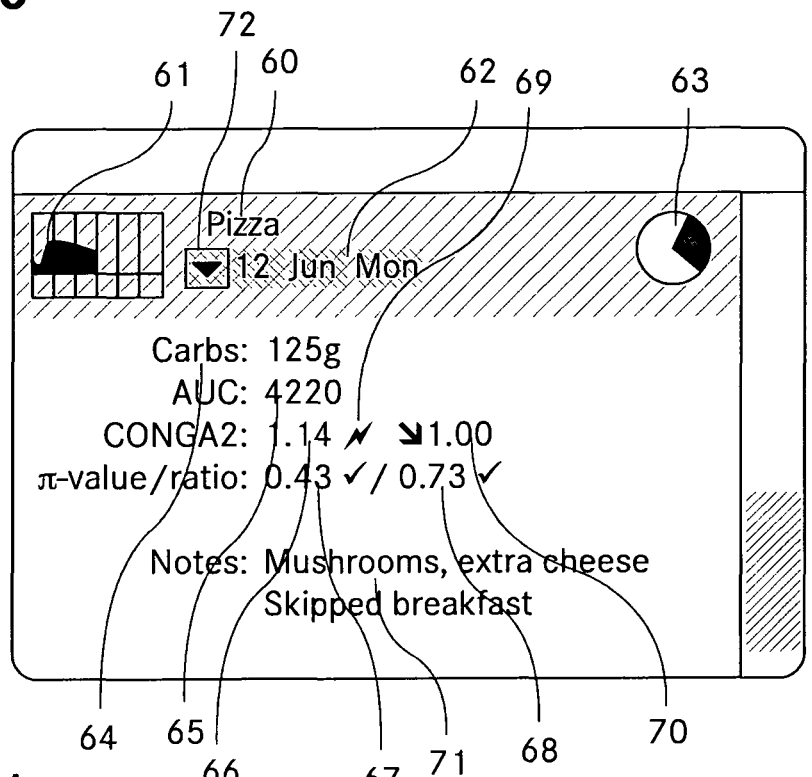
FIG. 11 the detailed view of an archived record.

FIG. 11 shows the detailed view of a record that appears once it has been chosen from the event directory displayed in FIG. 10. The detailed view shows the information discussed above in relation with FIG. 10, i.e. the name 60 of the record ("Pizza") as well as the shape 61 of the glucose progression, date/weekday 62 ("12 Jun Mon") and time/interval 63 of the incident that has been most recently recorded. In a lower part of the display additional information relating to the displayed incident is provided such as the amount of carbohydrates 64 of the meal ("Carbs 125 g") provided by the user and the elicited glycemic response 65 ("AUC: 422", in units of mg·min/dl). Furthermore, information on measures for glycemic variability is provided, namely the value 66 of CONGA2 ("1.14") and the values 67, 68 of the π-value and π-ratio, respectively ("0.43/0.73") as well as information 69 on a comparison with a reference value and—if the values are not within target ranges—the respective target value 70 ("1.00").

Finally, notes 71 are displayed that are provided by the user (e.g. further information concerning the ingredients of the meal or concerning special circumstances, in the given example "Notes: Mushrooms, extra cheese, Skipped Breakfast"). The notes 71 may be provided or amended at any time. However, in order to ensure accurate information, the user will be prompted for the information immediately after creation of the record.

By default the most recently recorded incident is displayed. However, previous incidents of the same event may be easily accessed by means of a pulldown menu 72.

Further useful features of a graphical user interface which is suitable for the current invention are described in EP 06 405 457.0 (filed 31 Oct. 2006, F. Hoffmann-La Roche AG).

The disclosed system and method is not restricted en to the embodiments discussed above. Particularly, the glucose values may be obtained otherwise, e. g. by usual spot blood glucose measurements. Further (or modified) metrics or display modes for the results may be employed.

In summary, it is to be noted that a system and method for monitoring individual metabolic response that is comfortable for the user and that provides a personalized and specific feedback supporting the user's dietary management is disclosed herein.

The invention claimed is:

1. A method for monitoring individual metabolic response and for generating nutritional feedback, involving monitoring of a glucose level in a qualified subject, the method comprising:
  a) self-calibrating a glucose measuring device to establish a glucose reference level, wherein the glucose reference level corresponds to a fasting glucose level of the qualified subject;
  b) consecutively performing a plurality of measurements of a glucose level in the qualified subject by the glucose measuring device;
  c) generating first data in the glucose measuring device, the first data corresponding to the measured glucose level;
  (d) transmitting the first data to an analysis device;
  (e) generating second data in the analysis device, the second data representing at least one measure for variability of a glucose level of the qualified subject from a time-series of glucose measurements represented by the first data;
  (f) comparing the second data with reference data and further processing a result of the comparison for generating a conclusion about nutritional quality of foodstuffs consumed by the qualified subject and/or about a risk of long-term health complications of the qualified subject; and
  (g) providing feedback corresponding to the conclusion on an output device.

2. The method of claim 1, wherein the at least one measure for variability is calculated for first data representing two different time intervals yielding a first result and a second result and in that the first result and the second result are considered for comparing the second data with the reference data and for further processing the result of the comparison for generating the conclusion.

3. The method of claim 1 further comprising providing suggestions regarding how to achieve personal metabolic goals, the suggestions including suggestions about recommended type, portion size and/or timing of food ingestion.

4. The method of claim 1, wherein the glucose reference level is used for generating the second data and/or for comparing the second data with the reference data.

5. The method of claim 1, wherein generating the second data comprises calculating a mean value and/or a standard deviation of glucose level measurements represented by the first data and/or of quantities derived from the first data.

6. The method of claim 5, wherein generating the second data comprises calculating a standard deviation of a slope of a function representing the time-series of glucose measurements represented by the first data.

7. The method of claim 1, wherein generating the second data comprises calculating a difference between a first glucose measurement taken in the morning and a second glucose measurement taken in the evening preceding or following said morning, wherein both glucose measurements are represented by the first data.

8. The method of claim 1, further comprising:
  defining at least two glucose ranges, and
  classifying the glucose measurements represented by the first data the range in which the glucose measurements fall, wherein the classifications of a plurality of measurements are employed for generating the second data.

9. The method of claim 1, wherein generation of the second data comprises determining values in phase space coordinates from the time-series of glucose measurements represented by the first data, wherein the phase space values are further processed and/or displayed on the output device.

10. The method of claim 1, wherein the time-series of glucose measurements is selected corresponding to a time interval specified by user input.

11. The method of claim 1, wherein the time-series of glucose measurements is selected corresponding to a time interval that is automatically determined based on the first data, the time interval corresponding to a time interval relating to a single meal, determined by detecting a rise from a glucose reference level and a return to the glucose reference level.

12. The method of claim 1, wherein further processing the result of the comparison comprises considering additional information, the additional information including at least one of: timing of ingested foodstuffs, quantity of ingested foodstuffs, type of ingested foodstuffs, physical activity of the qualified subject, and values of physiological parameters of the qualified subject, wherein the additional information is received from one of: another device and user input.

13. The method of claim 1, wherein the second data comprises at least one metric for glycemic variability selected from the group consisting of:
   a) M-value;
   b) Pi-index;
   c) coefficient of variation;
   d) J-index;
   e) MODD;
   f) CONGA;
   g) Stability parameter;
   h) Low BG index (LBGI), High BG index (HBGI) and/or CGM/BG risk index; and
   i) average daily risk range (ADRR).

14. The method of claim 1, further comprising:
   a) generating third data representing a measure for a quantity of glycemic response of the qualified subject from the time-series of glucose level measurements represented by the first data, the third data being an area-under-the-curve (AUC) value;
   b) comparing the third data with a predetermined individual glycemic response budget for the qualified subject, the individual glycemic response budget representing a total amount of individual glycemic response allowable for a certain time period.

15. The method of claim 14, wherein a result of the comparison of the third data with the predetermined individual glycemic response budget is considered for comparing the second data with the reference data and/or for further processing the result of the comparison for generating the conclusion.

16. The method of claim 1, wherein providing feedback on the output device comprises receiving user interaction used to control interpretation of the second data.

17. The method of claim 1, further comprising correcting a raw signal corresponding to the measured glucose level against drift, signal instability, or a system error of the glucose measuring device.

18. A glucose monitoring system for monitoring glycemic individual metabolic response in a qualified subject and for generating nutritional feedback, comprising:
   a) a glucose measuring device comprising a sensor for consecutively performing a plurality of measurements of a glucose level in the qualified subject and comprising a data generator for generating first data corresponding to the measured glucose level, wherein the glucose measuring device is configured to self-calibrate to establish a glucose reference level, wherein the glucose reference level corresponds to a fasting glucose level of the qualified subject;
   b) an analysis device comprising a computer to generate second data representing at least one measure for variability of the glucose level of the qualified subject from a time-series of glucose measurements represented by the first data, and to compare the second data with reference data and for further processing a result of the comparison for generating a conclusion about nutritional quality of foodstuffs consumed by the qualified subject and/or about a risk of long-term health complications of the qualified subject; and
   c) a computer-controlled output device to provide feedback corresponding to the conclusion.

19. The system of claim 18, wherein the glucose measuring device is an implantable glucose sensor.

20. The system of claim 19, wherein the glucose measuring device comprises a storage for temporarily storing the first data and the glucose measuring device and the analysis device each comprises transmission components for off-loading of the accumulated stored first data to the analysis device, in particular after the glucose measuring device has been removed from the body of the qualified subject.

21. The system of claim 18, wherein the glucose measuring device and the analysis device each comprise transmission components for transmitting the first data from the glucose measuring device to the analysis device via a wireless link and the analysis device comprises a storage for storing the received first data.

22. The system of claim 18, wherein the analysis device and the output device are incorporated in a handheld device.

23. The system of claim 18, wherein the analysis device comprises a storage for storing the reference data for the qualified subject.

24. The system of claim 18, wherein the glucose measuring device and the analysis device each comprises an electronic circuit for correcting a raw signal corresponding to the measured glucose level against at least one of drift, signal instability, and system error.

25. The system of claim 18, wherein at least one of the analysis device and the output device comprises a user input device programmed in such a way that a user may control interpretation of the second data by using the input device.

26. The system of claim 18, wherein the analysis device comprises a storage for storing second data as well as user-specified information.

27. The method of claim 1, wherein self-calibrating the glucose measuring device comprises self-calibrating the glucose measuring device without an independent glucose measurement.

* * * * *